US011834693B2

(12) United States Patent
Leuschner et al.

(10) Patent No.: US 11,834,693 B2
(45) Date of Patent: Dec. 5, 2023

(54) INTRON-BASED UNIVERSAL CLONING METHODS AND COMPOSITIONS

(71) Applicant: SANOFI, Paris (FR)

(72) Inventors: Wulf Leuschner, Frankfurt am Main (DE); Werner Dittrich, I, Frankfurt am Main (DE); Joerg Birkenfeld, Frankfurt am Main (DE); Marion Schneider, Frankfurt am Main (DE)

(73) Assignee: SANOFI, Paris (FR)

( * ) Notice: Subject to any disclaimer, the term of this patent is extended or adjusted under 35 U.S.C. 154(b) by 887 days.

(21) Appl. No.: 16/576,511

(22) Filed: Sep. 19, 2019

(65) Prior Publication Data

US 2020/0115728 A1 Apr. 16, 2020

(30) Foreign Application Priority Data

Sep. 20, 2018 (EP) .................................... 18306220

(51) Int. Cl.
*C12P 19/34* (2006.01)
*C12N 15/85* (2006.01)

(52) U.S. Cl.
CPC .............. *C12P 19/34* (2013.01); *C12N 15/85* (2013.01)

(58) Field of Classification Search
CPC ..... C12P 19/34; C12N 15/85; C12N 2830/42; C12N 15/66; C12N 15/1031; C12N 9/22; C12Q 2521/313; C12Q 2521/501; C07K 2319/50
See application file for complete search history.

(56) References Cited

U.S. PATENT DOCUMENTS

| | | |
|---|---|---|
| 2004/0241852 A1 | 12/2004 | Heiermann |
| 2014/0242637 A1* | 8/2014 | Enenkel ................. C12N 15/85 435/69.6 |
| 2016/0032295 A1 | 2/2016 | Minshull et al. |
| 2017/0152520 A1 | 6/2017 | Moellering et al. |

FOREIGN PATENT DOCUMENTS

| | | |
|---|---|---|
| EP | 2395087 A1 | 12/2011 |
| EP | 3401328 A1 | 11/2018 |
| WO | WO 2008/095927 A1 | 8/2008 |
| WO | WO 2010/140066 A2 | 12/2010 |

OTHER PUBLICATIONS

Endy, "Foundations for engineering biology", Nature, 438(24):449-453 doi:10.1038/nature04342, Nov. 2005.
Engler and Marillonnet, "Golden gate cloning", DNA Cloning and Assembly Methods, Methods in Molecular Biology, vol. 1116, Chapter 9, pp. 119-131, Svein Valla and Rahmi Lale (eds), Humana Press, New York, 2014.
Engler et al., "A One Pot, One Step, Precision Cloning Method with High Throughput Capability", Plos ONE 3(11): e3647.doi:10.1371/journal.pone.0003647, Nov. 5, 2008.
Engler et al., "Golden Gate Shuffling: A One-Pot DNA Shuffling Method Based on Type IIs Restriction Enzymes", Plos ONE 4(5): e5553. doi:10.1371/journal.pone.0005553, May 14, 2009.
Gatermann et al., "Introduction of Functional Artificial Introns into the Naturally Intronless ura4 Gene of Schizosaccharomyces pombe", Molecular and Cellular Biology, vol. 9, No. 4, pp. 1526-1535 doi:10.1128/mcb.9.4.1526, Apr. 1989.
Hong et al., "Intron Size, Abundance, and Distribution Within Untranslated Regions of Genes", Molecular Biology and Evolution, 23(12): 2392-2404, Sep. 15, 2006.
Jäger et al., "High level transient production of recombinant antibodies and antibody fusion proteins in HEK293 cells", BMC Biotechnology, 13:52, Jun. 26, 2013.
Knight, "Idempotent Vector Design for Standard Assembly of Biobricks", MIT Artificial Intelligence Laboratory; MIT Synthetic Biology Working Group, doi: 1721.1/21168, 2003.
Lacy-Hulbert et al., "Interruption of coding sequences by heterologous introns can enhance the functional expression of recombinant genes", Gene Therapy vol. 8, pp. 649-653, Jan. 30, 2001.
Lee and Rio, "Mechanismas and Regulation of Alternative Pre-Mrna Splicing", Annu Rev Biochem. vol. 84, pp. 291-323. doi:10.1146/annurev-biochem-060614-034316, Jun. 2015.
Nuñez-Prado et al., "The coming of age of engineered multivalent antibodies", Drug Discovery Today, vol. 20, No. 5, pp. 588-594. doi: 10.1016/j.drudis.2015.02.013, May 2015.
Sarrion-Perdigones et al., "GoldenBraid: An Iterative Cloning System for Standardized Assembly of Reusable Genetic Modules", Plos ONE, vol. 6, Issue 7, e21622 doi:10.1371/journal.pone.0021622, Jul. 7, 2011.
Shefer et al., "The Supraspliceosome—A Multi-Task machine for Regulated Pre-Mrna Processing in the Cell Nucleus", Computational and Structural Biotechnology Journal vol. 11, pp. 113-122, Sep. 2014.
Shimada et al., "Identification and Validation of Evolutionarily Conserved Unusually Short Pre-mRNA Introns in the Human Genome", Int. J. Mol. Sci. vol. 16, pp. 10376-10388; doi:10.3390/ijms160510376, May 7, 2015.

(Continued)

*Primary Examiner* — Paul J Holland
(74) *Attorney, Agent, or Firm* — LATHROP GPM LLP; James H. Velema, Esq.

(57) ABSTRACT

The present invention relates to a method for producing a fusion polynucleotide encoding a polypeptide of interest. The method comprises the steps of providing a first polynucleotide and a second polynucleotide, and contacting said first polynucleotide and second polynucleotide with a type IIs restriction endonuclease and a ligase under conditions that allow for the cleavage of the first polynucleotide and second polynucleotide by said type IIs restriction endonuclease and the ligation of the resulting cleavage products, thereby producing the fusion polynucleotide encoding the polypeptide of interest. The first polynucleotide comprises the 5' portion of an intron, and the second polynucleotide comprises the 3' portion of an intron. Further envisaged by the present invention is a polynucleotide encoding a polypeptide of interest, which, when transcribed in a eukaryotic host cell, is transcribed into a transcript comprising at least five introns which are heterologous to said polynucleotide.

12 Claims, 8 Drawing Sheets

Specification includes a Sequence Listing.

(56) References Cited

OTHER PUBLICATIONS

Sperling, "The nuts and bolts of the endogenous spliceosome", WIREs RNA 2016.doi:10.1002/wrna.1377, 2016.

Vancanneyt et al: "Construction of an intron-containing marker gene: splicing of the intron in transgenic plants and its use in monitoring early events in agrobacterium-mediated plant transformation", Molecular and General Genetics, vol. 220, No. 2, pp. 245-250, XP008075800, ISSN: 0026-8925, DOI: 10.1007/BF00260489.

Weber et al., "A Modular Cloning System for Standardized Assembly of Multigene Constructs", Plos ONE vol. 6, Issue 2, e16765. doi:10.1371/journal.pone.0016765, Feb. 2011.

Xiao et al., "A Novel Dual Expression Platform for High Throughput Functional Screening of Phage Libraries in Product like Format", Plos ONE 10(10): e0140691. doi:10.1371/journal.pone. 0140691, Oct. 15, 2015.

Yan et al, "High-Throughput Construction of Intron-Containing Hairpin RNA Vectors for RNAi in Plants", Plos ONE, vol. 7, No. 5, e38186, XP055253591, DOI: 10.1371/journal, pone.0038186, May 31, 2012.

Yeo et al., "Discovery and Analysis of Evolutionarily Conserved Intronic Splicing Regulatory Elements", PLOS Genetics, vol. 3, Issue 5, e85 doi:10.1371/journal.pgen.0030085, May 2007.

\* cited by examiner

Light Chain

Heavy Chain

US 11,834,693 B2

INTRON-BASED UNIVERSAL CLONING METHODS AND COMPOSITIONS

RELATED APPLICATION

This application claims the benefit of European Patent Application No. 18306220.7, filed Sep. 20, 2018, the entire disclosure of which is hereby incorporated herein by reference.

BACKGROUND OF THE INVENTION

Recombinant DNA molecules and molecular cloning methods that allow for assembly of multiple DNA fragments into a single contiguous stretch of DNA are essential tools for molecular biology, biotechnology and medical research. The first recombinant DNA molecule was made in the late 1960s, shortly after the discovery of restriction enzymes and DNA ligases. Since then, various methods have been developed to speed-up and facilitate the generation of recombinant DNA molecules.

Protein engineering is typically done by manipulating the underlying coding DNA sequences. Directional assembly of DNA modules coding for different protein domains is central to the development and optimization of novel biotherapeutic formats.

Molecular cloning has progressed from the cloning of a single DNA fragment to the assembly of multiple DNA components into a single contiguous stretch of DNA. However, there is still a need for efficient technologies that allow for the generation of complex constructs (see Endy, Nature 2005 Nov. 24; 438(7067):449-53). In particular, a set of standard and reliable engineering mechanisms is desired in order to remove much of the tedium and surprise during assembly of genetic components into larger systems (see Knight, T. F. (2003). Idempotent Vector Design for Standard Assembly of Biobricks. DOI: 1721.1/21168).

DNA modules (e.g. coding for protein domains) are typically assembled by cut-and-paste mechanisms using defined flanking prefix and suffix DNA sequences. Classically, prefix and suffix sequences are coding for palindromic type II restriction sites. Type II enzymes recognize and cleave DNA at the same site and create single-stranded overhangs which can be fused to other DNA modules which are cut by the same restriction enzyme. However, DNA modules of interest have to be 5' and 3' terminally equipped with suitable type II restriction sites by means of DNA manipulation techniques resulting in altered/mutated primary nucleotide sequences. Further, linear, directional DNA module assembly requires several, unique type II sites. Assembly usually requires several cloning steps as different type II restriction enzymes are often not compatible with regard to reaction conditions.

Golden Gate cloning is a frequently used molecular cloning method that allows simultaneous and directional assembly of multiple DNA fragments into a single piece using type IIs restriction enzymes and T4 DNA ligase. Engler 2008, A one pot, one step, precision cloning method with high throughput capability. PloS ONE 3.11: e3647, and Engler et al. 2009, Golden gate shuffling: a one-pot DNA shuffling method based on type IIs restriction enzymes. PLoS ONE 4: e5553. Unlike standard type II restriction enzymes such as EcoRI and BamHI, type IIs restriction enzymes such as BsaI, BsmBI and BbsI, cut DNA outside of their recognition sequence and therefore can create non-palindromic overhangs. With proper design of the cleavage sites, two fragments cut by type IIs restriction enzymes can be ligated into a product lacking the original restriction site.

Type IIs-based restriction-ligation allows for assembly of many DNA fragments in a single cloning step. For assembly, DNA fragments require stretches of 1 to 6 bp long, e.g. 3-4 bp long, complementary sequences at their 5' (prefix) and 3' (suffix) ends flanked by type IIs enzyme recognition sites in a defined distance and orientation. Upon binding to recognition sites, type IIs enzymes cleave DNA fragments at prefix and suffix nucleotide sequences, thereby removing the actual recognition site, and at the same time generating free 5' and 3' ends consisting of the ligation sequences. These ligation sequences are then used to fuse together DNA fragments with matching/compatible ligation sequences in a ligation reaction. Consequently, if 5' prefix and 3' suffix sequences are identical between two distinct DNA fragments, these fragments can be seamlessly ligated in type IIs-based restriction-ligation reactions.

In general, DNA fragments/modules that have been used to generate a particular variant library cannot be re-used (i.e. re-assembled) in the context of a new project as they often do not display compatible prefix and suffix sequences. Instead, modules need to be redesigned to match the different cloning strategies (i.e. that prefix and suffix sequences need to be adapted to allow for ligation). This is a very time-consuming and costly aspect, especially since frequently the 4 bp prefix and suffix sequences of the DNA fragments/modules need to be modified while the prefix- and suffix-flanked core sequences stay unaltered.

Thus, a major limitation of the cloning strategies described in the art is that they still require unique and compatible prefix and suffix sequences within the DNA modules to allow for directional assembly. These prefix and suffix sequences may not be compatible between different protein domains and/or formats which limits the universal applicability of these methods.

To date, no efficient method exists to generate generic DNA fragment modules that could be re-used and assembled in type IIs-based restriction-ligation reactions independent of their 5' and 3' prefix and suffix sequences.

Pre-mRNA splicing is an essential process in eukaryotic gene expression. In higher vertebrates, the length of target introns that need to be recognized range from <50 nt to >500.000 nt. In humans, introns with a length of about 90 nt to about 2000 nt are most commonly found within a pre-mRNA. However, also short or even ultra-short intron sequences have been described. For example, short introns have been found in *C. elegans* (<40 nt), *Arabidopsis thaliana* (~20-59 nt) and in human tissue (<65 nt) (Hong et al. 2006, Intron size, abundance, and distribution within untranslated regions of genes. Molecular biology and evolution, 23(12), 2392-2404; Shimada et al., 2015, Identification and validation of evolutionarily conserved unusually short pre-mRNA introns in the human genome. Int. J. Mol. Sci. 2015, 16, 10376-10388).

Introns located at the boundaries between introns and exons in a pre-mRNA are also referred to as spliceosomal introns. RNA splicing removes the non-coding RNA introns leaving behind the exons, which are then spliced and joined together to form the final mRNA ("mature mRNA").

There remains a strong need for the fast and easy generation of recombinant DNA molecules that allows for expression of multiple genes of interest. Especially means and methods to generate generic DNA fragment modules that could be re-used and assembled in type IIs-based restriction-ligation reactions independent of their 5' ends and 3' ends, i.e. prefix and suffix sequences, would be highly desirable.

SUMMARY OF THE INVENTION

The technical problem underlying the present invention can be seen as the provision of means and methods for complying with the aforementioned needs. The technical problem is solved by the embodiments characterized in the claims and herein below.

Accordingly, in certain aspects, the present invention relates to a method for producing a fusion polynucleotide encoding a polypeptide of interest. In certain embodiments, said method comprises contacting a first and a second polynucleotide with the type IIs restriction endonuclease and a ligase under conditions that allow for cleavage of the first polynucleotide and the second polynucleotide by said type IIs restriction endonuclease and ligation of the resulting cleavage products, thereby generating the fusion polynucleotide encoding the polypeptide of interest. In certain embodiments, each of said first and said second polynucleotide comprises an intron sequence comprising a recognition and cleavage site for a type IIs restriction endonuclease which upon cleavage generates complementary ends which can be ligated to each other such that the fusion polynucleotide encoding the polypeptide of interest is produced. In certain embodiments, the first polynucleotide comprises the 5' portion of an intron and the second polynucleotide comprises the 3' portion of an intron.

In another aspect, the present invention further relates to a composition comprising a first, second and third polynucleotide. Further envisaged by the present invention is a polynucleotide encoding a polypeptide of interest, which, when transcribed in a eukaryotic host cell, is transcribed into a transcript comprising at least five introns which are heterologous to said polynucleotide.

In an embodiment of the aforementioned method, the first polynucleotide comprises, in 5' to 3' direction, the following elements:
  (i) a nucleic acid sequence encoding a first portion of the polypeptide of interest,
  (ii) a nucleic acid sequence encoding a 5' portion of a first intron,
  (iii) a first cleavage sequence for a type IIs restriction endonuclease, and
  (iv) a recognition sequence for said type IIs restriction endonuclease, wherein the cleavage sequence in (iii) is operably linked to the recognition sequence in (iv).

In an embodiment of the aforementioned method, the second polynucleotide comprises, in 5' to 3' direction, the following elements:
  (i) a recognition sequence for the type IIs restriction endonuclease,
  (ii) a second cleavage sequence for the type IIs restriction endonuclease, wherein said second cleavage sequence is complementary to the first cleavage sequence, wherein the second cleavage sequence in (ii) is operably linked to the recognition sequence in (i), i.e. to the recognition sequence of the second polynucleotide,
  (iii) a nucleic acid sequence encoding a 3' portion of the first intron, and
  (iv) a nucleic acid sequence encoding a second portion of the polypeptide of interest.

Thus, the present invention relates to a method for producing a fusion polynucleotide encoding a polypeptide of interest, said method comprising the steps of:
  (a1) providing a first polynucleotide, said first polynucleotide comprising, in 5' to 3' direction,
    (i) a nucleic acid sequence encoding a first portion of the polypeptide of interest,
    (ii) a nucleic acid sequence encoding a 5' portion of a first intron,
    (iii) a first cleavage sequence for a type IIs restriction endonuclease, and
    (iv) a recognition sequence for said type IIs restriction endonuclease, wherein the cleavage sequence in (iii) is operably linked to the recognition sequence in (iv), i.e. to the recognition sequence of the first polynucleotide
  (a2) providing a second polynucleotide, said second polynucleotide comprising, in 5' to 3' direction,
    (i) a recognition sequence for the type IIs restriction endonuclease,
    (ii) a second cleavage sequence for the type IIs restriction endonuclease, wherein said second cleavage sequence is complementary to the first cleavage sequence, wherein the second cleavage sequence in (ii) is operably linked to the recognition sequence in (i) i.e. to the recognition sequence of the second polynucleotide,
    (iii) a nucleic acid sequence encoding a 3' portion of the first intron, and
    (iv) a nucleic acid sequence encoding a second portion of the polypeptide of interest, and
  (b) contacting said first polynucleotide and second polynucleotide with the type IIs restriction endonuclease and a ligase under conditions that allow for cleavage of the first polynucleotide and the second polynucleotide by said type IIs restriction endonuclease and ligation of the resulting cleavage products, thereby producing the fusion polynucleotide encoding the polypeptide of interest.

The produced polynucleotide comprises a first intron, i.e. shall encode the first intron. Said first intron shall be functional and shall comprise the nucleic acid sequence encoding the 5' portion of the first intron and the nucleic acid sequence encoding the 3' portion of the first intron.

Accordingly, the produced fusion polynucleotide shall comprise, in 5' to 3' direction,
  (aa) the nucleic acid sequence encoding the first portion of the polypeptide of interest,
  (bb) a nucleic acid sequence encoding a first intron, wherein said first intron is functional, and wherein said first intron comprises the nucleic acid sequence encoding the 5' portion of the first intron and the nucleic acid sequence encoding the 3' portion of the first intron, and
  (cc) the nucleic acid sequence encoding the second portion of the polypeptide of interest.

The method of the present invention allows for the production of a fusion polynucleotide encoding a polypeptide of interest. Thus, the method is a cloning method. Such methods are typically carried out in vitro. The method of the present invention is not limited to the steps explicitly mentioned above and, thus, may comprise steps in addition to these steps. For example, further steps may relate to the ligation of additional polynucleotide sequences to the fusion polynucleotide of the present invention. E.g., as described herein below, the method of the present invention does not only allow for the production of a fusion polynucleotide comprising the elements (aa), (bb) and (cc) as set forth above, but also the production of a fusion polynucleotide comprising additional elements such as nucleic acid sequences encoding a the third, fourth, fifth, sixth, seventh, eighth, ninth, tenth etc. portion of the polypeptide of interest. Further, additional polynucleotides can be used for the ligation. Such polynucleotides may encode the 5' untranslated region (5' UTR) and 3' untranslated region (3' UTR) of the polynucleotide encoding the polypeptide of interest. Since these sequences are transcribed, but not translated, it is possible to apply the intron-based cloning approach as described herein.

Moreover, further steps may relate to the cloning of the fusion polynucleotide into a vector such as an expression vector, the introduction of the fusion polynucleotide, or the vector comprising said fusion polynucleotide into a suitable host cell such as a mammalian cell, and/or the isolation, i.e. the purification, of the polypeptide from the host cell or the culture medium/supernatant. The purification process might be supported by the presence of suitable tags in the protein of interest, e.g. a His tag.

The term "polynucleotide" as used herein shall refer to a ribonucleic acid (RNA), or in particular to a desoxyribonucleic acid (DNA). Unless stated otherwise, the term "polynucleotide" herein refers to a single strand of a DNA polynucleotide or, in particular to a double-stranded DNA polynucleotide. Said double-stranded DNA shall during step (b) of the method of the present invention temporarily comprise one or two single-stranded overhangs at the end(s). This is depending on the number of cleavage sequences, i.e. cleavage sites, present in the polynucleotide: if one cleavage site is present, the polynucleotide comprises one single-stranded overhang at one end, if two cleavage sequences are present, the polynucleotide comprises two single-stranded overhangs (one at each end). The overhangs result from cleavage with the type IIs endonuclease and allow for the ligation of fragments in a predetermined order (as described elsewhere herein).

The length of a polynucleotide is designated by the number of base pairs or nucleotides. Unless otherwise stated, both terms are used interchangeably, regardless whether or not the respective nucleic acid is a single- or double-stranded nucleic acid. Also, as polynucleotides are defined by their respective nucleotide sequence, the terms nucleotide/polynucleotide and nucleotide sequence/polynucleotide sequence are used interchangeably.

The polynucleotide that shall be produced by the present invention shall be a fusion polynucleotide and thus shall be produced by the fusion of various polynucleotides. In particular, said fusion polynucleotide shall be produced by contacting the first polynucleotide herein and second polynucleotide, and optionally, at least one further polynucleotide (such as a third, fourth, fifth, sixth, seventh, eighth, ninth, tenth etc. polynucleotide) with a type IIs restriction endonuclease and a ligase under conditions that allow for the cleavage of the first polynucleotide and second polynucleotide (and, if present, of the at least one further polynucleotide, such as the third, fourth, fifth, sixth, seventh, eighth, ninth, tenth etc. polynucleotide) by said type IIs restriction endonuclease and the ligation of the resulting cleavage products, thereby producing the fusion polynucleotide encoding the polypeptide of interest.

According to steps (a1) and (a2) of the method of the present invention, a first and second polynucleotide shall be provided. How to provide a polynucleotide is well known in the art. In an embodiment, the provided polynucleotides are derived from (i.e. produced by) polymerase chain reaction (PCR). In another embodiment, said polynucleotides are derived from (i.e. produced by) artificial gene synthesis. The same applies to the third, fourth, fifth, sixth, seventh, eighth, ninth, and tenth etc. polynucleotide as referred to herein elsewhere. In an embodiment, the provided polynucleotides are present in a vector, i.e. are comprised by a vector. In an alternative embodiment, the polynucleotides are provided as linear DNA fragments.

The first polynucleotide as referred to in step (a1) of the method of the present invention shall comprise, in 5' to 3' direction, the following elements
   (i) a nucleic acid sequence encoding a first portion of the polypeptide of interest,
   (ii) a nucleic acid sequence encoding a 5' portion of a first intron,
   (iii) a first cleavage sequence for a type IIs restriction endonuclease, and
   (iv) a recognition sequence for said type IIs restriction endonuclease, wherein the first cleavage sequence in (iii) is operably linked to the recognition sequence in (iv).

The second polynucleotide as referred to in step (a1) of the method of the present invention shall comprise, in 5' to 3' direction, the following elements
   (i) a recognition sequence for the type IIs restriction endonuclease
   (ii) a second cleavage sequence for the type IIs restriction endonuclease, wherein said second cleavage sequence is complementary to first cleavage sequence, wherein the second cleavage sequence in (ii) is operably linked to the recognition sequence in (i), i.e. to the recognition sequence of the second polynucleotide,
   (iii) a nucleic acid sequence encoding a 3' portion of the first intron, and
   (iv) a nucleic acid sequence encoding a second portion of the polypeptide of interest.

The nucleic acid sequence as set forth under item (i) of step (a1) shall encode a first portion of the polypeptide of interest, and the nucleic acid sequence under item (iv) of step (a2) for a second portion of said polypeptide. Typically, a nucleic acid sequence encoding shall encode a portion of the polypeptide of interest as referred to herein in accordance with the present invention has a length of at least 10, at least 50, or at least 200 bp. Said nucleic acid sequence shall comprise a portion of the coding sequence. Thus, the portion of the polypeptide may have a length of at least 1 amino acid, at least about 3 amino acids, at least about 15 amino acids, or at least about 50 amino acids. Thus, the portion may have a length from a minimum 1 amino acid to any feasible length, e.g. 100 amino acids, 500 amino acids, 1000 amino acids, or more. In an embodiment of the method of the present invention, the portion comprises a protein domain. Thus, the portion may have a length of e.g. 100 to 150 amino acids.

The nucleic acid sequence which encodes the first portion of a polypeptide may further comprise a 5' untranslated region (5' UTR). The polynucleotide which encodes the last portion of a polypeptide, i.e. the C-terminal end, may further comprise a 3' untranslated region (3' UTR).

The nucleic acid sequence encoding a first portion of the polypeptide of interest, preferably, is the first exon of the fusion polynucleotide. Thus, said nucleic acid sequence shall encode the first exon of the resulting transcript. The nucleic acid sequence encoding the second portion of the polypeptide of interest, preferably, is the second exon of the fusion polynucleotide. The nucleic acid sequence encoding the third portion of the polypeptide of interest, preferably, is the third exon of the fusion polynucleotide etc.

The exons comprised by the produced fusion polynucleotide are separated by functional introns. E.g., the first exon and the second exon are separated by a first intron. Further exons, if present in the fusion polynucleotide, are preferably separated by functional introns as well. Thus, if a third exon is present, the second exon and the third exon are separated by a second intron, and if a fourth exon is present, the third exon and the fourth exon are separated by a third intron, etc. In an embodiment, the introns comprised by the fusion polynucleotide are identical, i.e. have an identical sequence. In another embodiment, the introns comprised by the fusion polynucleotide have different sequences. In this embodiment, e.g. the introns of different genes and/or different organisms may be used. The introns may be also artificial introns, i.e. introns which do not occur in nature. E.g., artificial introns may be designed by combining the 5' and 3' portions from two different introns, or by mutating naturally occurring introns. Naturally occurring introns may be mutated by adding, replacing, or deleting one or more nucleotides. FIG. 7 shows that an intron which contains additional nucleotides can be efficiently spliced out from a transcript comprising said intron.

In accordance with the present invention, the fusion polynucleotide produced by the method of the present invention shall be expressed, i.e. transcribed, in a eukaryotic host cell in order to produce the polypeptide of interest. The unprocessed transcript that results from expression of the fusion polynucleotide, i.e. the precursor messenger RNA (pre-mRNA), shall comprise all exon and intron sequences encoded by the fusion polynucleotide. Said transcript is processed in the eukaryotic cell so that the intron (or the introns) is (are) spliced out of said transcript, thereby producing a messenger RNA (mRNA) encoding the polypeptide of interest, i.e. a mRNA that is translated into the polypeptide of interest. Since the introns are removed from precursor mRNA by splicing, the mRNA comprises the exon sequences only.

It has been shown in the studies underlying the present inventions that not all tested introns were spliced out of the generated transcripts. The method of the present invention may therefore comprise the further step of assessing whether (or not) the fusion polynucleotide produced by the method of the present invention allows for the production of the polypeptide of interest when expressed in a in a eukaryotic host cell. This assessment may be done by assessing the produced polypeptide (e.g. of its activity).

DETAILED DESCRIPTION OF THE INVENTION

Figure 1:
FIG. 1: Bi-cistronic vector (pcDNA5dual-FRT-TO_D-EST, based on pcDNA5-FRT-TO_DEST [Invitrogen/ThermoFisher Scientific] used for expression constructs.

The term "intron" is well known in the art. As used herein, the term refers to a nucleotide sequence present within an unprocessed transcript which nucleotide sequence is capable of being spliced, i.e. excised, from the transcript by a eukaryotic host cell. Said unprocessed transcript is frequently also referred to as precursor messenger RNA (pre-mRNA). The splicing of the intron from the unprocessed transcript occurs prior to translation of the processed transcript, i.e. the mature messenger RNA. In principle, any intron that is functional (in particular that is functional in the host cell in which the fusion polynucleotide as referred to herein shall be expressed) can be used. Such intron may be naturally occurring introns, or artificial introns, i.e. intron that do not occur in nature but which are functional. Artificial introns comprising functional splice sites were described e.g. by Gatermann et al., Mol. Cell Biol., 9:1526 (1989).

As set forth above, the intron(s) comprised by the fusion polynucleotide shall be functional. The term "functional" in connection with intron is well understood by the skilled person. An intron which is functional typically is an intron which is capable of being spliced out from a transcript (in particular from pre-mRNA) that is expressed in a eukaryotic host cell. Whether an intron is functional can be assessed by well known methods. E.g., it is possible to analyze the activity of the expressed protein in order to assess whether an intron has been spliced out, or not. The fusion polynucleotide, when transcribed in a eukaryotic host cell, is transcribed into a transcript that is processed in said cell so that the functional intron is spliced out of said transcript, thereby producing an mRNA encoding the polypeptide of interest. If the fusion polynucleotide comprises one or more further introns (such as a second intron), the further introns are spliced out of the transcript as well (to produce the mRNA encoding the polypeptide of interest).

In a preferred embodiment of the present invention, the term "intron" refers to a spliceosomal intron (sometimes referred to as nuclear pre-mRNA intron). As known in the art, spliceosomal introns comprise specific intron sequences located at the boundaries between introns and exons. These sequences are recognized by spliceosomal RNA molecules (see e.g. Sperling (2016): WIREs RNA 2016.doi: 10.1002/wrna.1377; Shefer et al. (2014): Comp. Struct. Biotechnol. J. 11, 113).

In an embodiment of the present invention, the intron that is functional comprises a splice donor site, a branchpoint, a polypyrimidine tract, and splice acceptor site. Said elements are well known in the art. The splice donor site consists of a GU (GT) sequence at the 5' end of the intron. The splice acceptor site is located at the 3' end of the intron and thus terminates the intron. Said acceptor site consists of an AG sequence. The branchpoint includes an adenine nucleotide involved in lariat formation. The polypyrimidine tract is rich with pyrimidine nucleotides and typically has a length of 15-20 nt. Typically, it is located about 5-40 nt before the 3' end of the intron to be spliced. The tract promotes the assembly of the spliceosome.

As used herein, the term "intron" refers to both the nucleic acid sequence which encodes the intron as well as the corresponding sequence in the transcript of said sequence.

An intron comprised by the fusion polynucleotide may have any length (as long as it is functional). In an embodiment of the method of the present invention, the nucleic acid encoding an intron (i.e. a functional intron comprising the ligated 5' and 3' portions of the intron) has a length of 40 to 2000 bp, in particular a length of 50 to 1000 bp. Thus, the intron(s) encoded by the fusion polynucleotide, i.e. the intron(s) comprised by the transcript (such as the first, second and/or third intron) shall have a length of 40 to 2000 nt, in particular of 50 to 1000 nt.

In an embodiment, the introns that are used in accordance with the present invention, i.e. the introns comprised by the transcript encoded by the fusion polynucleotide, are short introns. The use of such introns is advantageous because this will decrease the size of the fusion polynucleotide produced by the method of the present invention and make it easier to handle. Further, the synthesis of small introns by gene synthesis is associated with lower costs as compared to large introns. A short intron as referred to herein typically has a length of less than 500 nt. In an embodiment, the short intron has a length of 50 to 200 nt. In another embodiment, the short intron has a length of 50 to 150 nt. In a further embodiment, the short intron has a length of 50 to 100 nt. E.g., each of the introns present in the transcript may have a length of 50 to 200 nt, such as a length of 50 to 150 nt or a length of 50 to 100 nt. Thus, it is envisaged that the polynucleotide encoding an intron (i.e. a functional intron) has a length of 50 to 200 bp, in particular of 50 to 150 bp, or 50 to 100 bp.

Ultra-short introns that are functional have been described in the art. For example, ultra-short introns have been described by Shimada et al., 2015 (Identification and validation of evolutionarily conserved unusually short pre-mRNA introns in the human genome. Int. J. Mol. Sci. 2015, 16, 10376-10388).

It has been shown in the studies carried out in accordance with the present invention that combinations of introns longer than 80 nucleotides generally give rise to higher expression levels than those containing ultra-short introns (see e.g. results for introns 18 and 19 in the Examples section). In a preferred embodiment, the intron(s) of the produced polynucleotide, thus, has (have) a length of at least 80 nucleotides, in particular at least 90 nucleotides. In a preferred embodiment, the intron(s) have a length of 80 to 200 nt. In another embodiment, the intron(s) has a length of 80 to 150 nt. In a further embodiment, the intron, e.g. each of the introns present in the transcript, has a length of 80 to 120 nt. Further, it is envisaged that the intron(s) has (have) a length of 90 to 150 nt or 90 to 120 nt.

Preferably, the intron(s) encoded by the produced polynucleotides has (have) a length of n nucleotides, wherein n is an integer which cannot be divided by three. Accordingly, the intron(s), in particular each of the introns, encoded by the produced polynucleotides may has (have) a length of n nucleotides, wherein n is an integer which when divided by three does not result in an integer. For example, the intron(s) may have a length of 91, 92, 94, 95, 97, 98, 100, 101, 103, 104, 106, 107, 109, 110, 112, 113, 115, 116, 118 or 119 nt.

In an embodiment of the method of the present invention, the intron(s) to be used is (are) selected from the introns that were used in the studies underlying the present invention. In particular, the intron may be intron 12, 13, 14, IS, or 17 (such as 12, 14, IS or 17) and, in particular 18 or 19 as shown in Table 1 of the Examples section, or a functional variant thereof as shown in Table 2. The sequences of these introns are shown in Table 3 of the Examples section.

In an embodiment of the method of the present invention, the at least one intron comprised by the polynucleotide of the present invention (such as the first intron) comprises an internal stop codon in frame with the open reading frame of the nucleic acid sequence encoding the polypeptide of interest. Thus at least one intron may comprise one or more in-frame stop codons. Further, it is envisaged, if the fusion polynucleotide comprises more than one intron (such as the first and second intron), that all introns comprise an internal stop codon in frame with the open reading frame of the nucleic acid sequence encoding the polypeptide of interest. Accordingly, each intron of the polynucleotide may comprise one or more internal stop codons in frame with the open reading frame of the nucleic acid sequence encoding the polypeptide of interest. The presence of one or more internal stop codons will result in the production of a truncated polypeptide in case of incomplete splicing. Such truncated polypeptides could be separated from the polypeptide of interest because of their shorter length.

Stop codons in RNA are e.g. UAG (amber), UAA (ochre), UGA (opal). The corresponding DNA sequences are TAG, TAA and TGA.

In some embodiments, the intron(s) comprises (comprise) at least one stop codon in each open reading frame of the polynucleotide encoding the fusion polypeptide as described herein. Thus, the one or more introns may comprise at least one stop codon in all three open reading frames.

As already explained elsewhere herein, the functional intron comprised by the fusion polynucleotide produced by the method of the present invention comprises the nucleic acid sequence encoding the 5' portion of an intron (e.g. of the first intron) and the nucleic acid sequence encoding the 3' portion of an intron (e.g. of the first intron). The functional intron(s) comprised by the fusion polynucleotide produced by the method of the present invention shall be generated by combining a 5' end of a functional intron and a 3' end of a functional intron. The combination is achieved in step (b) of the method of the present invention via compatible, i.e. complementary, overhangs that result from cleavage of the first, second (and if present the third, fourth, fifth etc.) polynucleotide with the type IIs restriction endonuclease. The cleavage and the ligation are preferably carried out simultaneously. Thus, the polynucleotides are combined by the so-called Golden Gate cloning, i.e. the fusion of the fragments in desired order in a reaction comprising the cleavage of the polynucleotides by a type IIs restriction endonuclease and ligation of the cleavage products in the presence of both a type IIs restriction endonuclease (i.e. an active type IIs restriction endonuclease) and a ligase.

In accordance with the present invention, it is envisaged that the 5' portion and the 3' portion of an intron as referred to herein are not functional, i.e. are not functional introns. Preferably, said portions of the intron do not comprise all elements required for being spliced out from a transcript. In accordance with the present invention, it is envisaged that the nucleic acid sequence encoding the 5' portion of an intron does not comprise the splice acceptor site. Said site shall be comprised by nucleic acid sequence encoding the 3' portion of the intron. Further, it is envisaged that the nucleic acid sequence encoding the 3' portion of an intron does not comprise the splice donor site. Said site shall be comprised by nucleic acid sequence encoding the 5' portion of the intron.

Since not all elements required for splicing are present, said portions, when present in a transcript alone, i.e. without the corresponding 5' or 3' portion, are not capable of being spliced out from the transcript. Functionality of the intron is achieved by ligating two polynucleotides comprising the 5' portion and 3' portion of the intron, respectively, as described elsewhere herein.

The sequence encoding the 5' and the 3' portion of an intron may have any length deemed suitable. The minimum length of the portion is the length of the overhang generated by cleavage with the restriction endonuclease that is applied in the method of the present invention. In an embodiment, the 5' portion of an intron comprises at least the splice donor site and the 3' portion of the intron comprises at least the splice acceptor site. Typically, the 5' portion and the 3' portion each have a length of at least 10 nt or at least 20 nt. The length of the portions tested in the Examples section was from 12 nt to 98 nt (see Table 4).

In an embodiment of the method of the present invention, the 5' and 3' portions on an intron are derived from a single intron. In another embodiment of the method of the present invention, the 5' and 3' portions of an intron are derived from two different introns. Thus, by assembling the polynucleotides as referred to herein, an artificial intron is generated.

In an embodiment of the present invention, at least one functional intron (such as the first intron), as referred to herein, is heterologous to a naturally occurring polynucleotide encoding the polypeptide of interest. In an embodiment of the present invention, the functional intron (such as the first intron), the functional introns, and/or the 5' and/or the 3' portions of an intron as referred to herein is/are heterologous to the fusion polynucleotide encoding the polypeptide of interest. Accordingly, the fusion polynucleotide might not have the sequence of a naturally occurring polynucleotide. In an embodiment of the present invention, the functional intron (such as the first intron), the functional introns, and/or the 5' and/or the 3' portions of an intron as referred to herein is/are heterologous to a naturally occurring polynucleotide encoding the polypeptide of interest. A polynucleotide (such as the intron(s), or portions thereof) that is heterologous to the fusion polynucleotide, preferably, is a polynucleotide that is not a naturally occurring polynucleotide (e.g. intron or portion thereof) in the fusion polynucleotide. In an embodiment, all introns (such as the first, second, third etc. intron) comprised by the fusion polynucleotide are heterologous to the fusion polynucleotide.

The same applies to the 5' portions and the 3' portions of the introns as referred to herein, i.e. it is envisaged that said portions are heterologous to the polynucleotides by which they are comprised. In particular, the nucleic acid sequence encoding the 5' portion or the 3' portion of an intron shall be heterologous to the nucleic acid sequence encoding the portion of the polypeptide of interest. For example, the nucleic acid sequence encoding the 5' portion of the first intron shall be heterologous to the nucleic acid sequence encoding the first portion of the polypeptide of interest, or the nucleic acid sequence encoding a 3' portion of the first intron shall be heterologous to the nucleic acid sequence encoding a second portion of the polypeptide of interest.

Further, it is envisaged that the functional intron (the functional introns) is (are) located at a position of the fusion polynucleotide (at positions of the fusion polynucleotide) which do not naturally (i.e. when it is in its biological genomic environment) comprise an intron.

The first, second, third, fourth, fifth etc. polynucleotide encoding a portion of the polypeptide of interest shall comprise at least one cleavage sequence for a type IIs restriction endonuclease, and at least one recognition sequence for the type IIs restriction endonuclease. The type IIs restriction endonuclease is used in combination with a ligase in step (b) of the method of the present invention for the production of the fusion polynucleotide. The production is achieved by assembling the various polynucleotides in a predetermined order.

The term "type IIs restriction endonuclease" is well understood by the skilled person. As used herein, the term refers to an endonuclease (frequently also referred to as "restriction enzyme") that cleaves DNA outside of its recognition sequence. Type IIs enzymes are known to cleave the DNA in a distance from 0 to 20 bp from its recognition sequence. A type IIs restriction endonuclease to be used in accordance with the method of the present invention, preferably, recognizes asymmetric, double-stranded DNA sequences, and cleaves the double-stranded DNA outside of the recognition sequence on the double-stranded DNA. Single-stranded overhangs ("sticky ends" are created by cleavage with the endonuclease. The overhang created by the endonuclease to be used in accordance with the method of the present invention typically has a length of 3, 4, 5 or 6 nucleotides. As known by the skilled person, this depends on the specificity of the used type IIs restriction endonuclease. However, production of longer overhangs by certain type IIs restriction endonucleases is also possible. In an embodiment, the type IIs restriction endonuclease shall, upon cleavage, create an overhang of 3 nucleotides. In another embodiment, it shall create an overhang of 4 nucleotides. For endonucleases that create overhangs of 4 bp, 256 (i.e., $4^4$) potential overhang sequences are possible. Thus, up to 256 polynucleotides can be assembled in a correct order.

Because type IIs restriction endonucleases cleave a DNA in a cleavage sequence (herein also referred to as "cleavage site") which is outside of, i.e. not comprised by, its recognition sequence (herein also referred to as "recognition site"), the first, second, third etc. polynucleotides provided in step (a) of the aforementioned method of the present invention comprise both a recognition sequence and a cleavage sequence. The cleavage sequence shall be operably linked to the recognition sequence. This means that the polynucleotide is cleaved at the cleavage site by the endonuclease after the endonuclease has recognized the recognition sequence in the polynucleotide.

It is known in the art that cleavage will occur only at a defined distance between the cleavage site and the recognition site. For example, most type IIs restriction endonucleases (but not all) require the presence of a spacer between the recognition sequence and the cleavage sequence. Thus, a spacer has to be present between the recognition sequence and a cleavage sequence (if the endonuclease requires a spacer). The spacer consists of one or more nucleotides. The length of the spacer depends on the applied restriction endonuclease. For example, BsaI cleaves one strand after one nucleotide (in 5' to 3' direction). Thus, a spacer of one nucleotide has to be present between the recognition sequence and the cleavage sequence in order to allow for cleavage at the cleavage site by this enzyme. Other endonucleases may require a longer spacer. E.g., if the applied endonuclease were to be FokI, a spacer having a length of nine nucleotides would be required.

Further, it is known in the art that some type IIs restriction endonucleases may be methylation sensitive and, thus, are not able to cleave at methylated-cytosine residues, leaving methylated DNA intact. In order to avoid that the type IIs enzyme's activity is blocked by methylated sequences in or around their respective recognition sequence, the polynucleotide to be cleaved is extended by one or two nucleotides such that potential known methylation sites are avoided. If the recognition site is located at the 5' end of the polynucleotide, the additional nucleotide(s) is (are) added to 5' end of the polynucleotide. If the recognition site is located at the 3' end of the polynucleotide, the additional nucleotide(s) is (are) added to 3' end of the polynucleotide. Thus, the polynucleotides described herein may further comprise one or two nucleotides at the 5' end or 3' end (depending on the location of the recognition site).

The recognition sequence is the sequence which is recognized by the type IIs endonuclease. The cleavage sequence is preferably the sequence which is cleaved in the presence of said endonuclease, i.e. which is capable of being cleaved by said endonuclease. It is to be understood that the recognition site has to be in correct orientation in order to allow for the cleavage at the cleavage site and the subsequent ligation. As will be understood by the skilled person, the orientation of the recognition site depends on whether cleavage shall occur at the 5' or 3' end of the polynucleotide. At the 5' end, cleavage shall occur in 5' to 3' direction. At the 3' end, cleavage shall occur in 3' to 5' direction.

In accordance with the present invention, the cleavage sequence(s) and recognition sequences comprised by the polynucleotide as referred to in step (a) of the method for producing a fusion polynucleotide thus shall be arranged that upon cleavage with the endonuclease the recognition sequence(s) is (are) removed from said polynucleotide (e.g. the first, second, third etc. polynucleotide). This is achieved by placing the recognition sequence(s) in the correct orientation with respect (i.e. upstream or downstream) to the cleavage sequence. E.g., the recognition sequence(s) could be placed in the correct orientation at the end(s) of said polynucleotide. Thus, if a polynucleotide as referred to herein shall be cleaved at the 5' end, the recognition sequence for the type IIs restriction endonuclease shall be located at the 5' end of said polynucleotide followed by the cleavage sequence. Thus, the cleavage sequence is located downstream from said recognition sequence. If a polynucleotide as referred to herein shall be cleaved at the 3' end, the recognition sequence for the type IIs restriction endonuclease shall be located at the 3' end of said polynucleotide. In this case, the cleavage sequence is located upstream from said recognition sequence. It is to be understood that it is not required to place the recognition sequence(s) at the end(s) of said polynucleotide. Rather, additional nucleotides may be present. E.g., additional nucleotides could be added to the 3' end of the polynucleotide.

In polynucleotides comprising a nucleic acid sequence encoding a 5' portion of an intron, the cleavage sequence for the type IIs restriction endonuclease shall be followed by the recognition sequence for said type IIs restriction endonuclease. In polynucleotides comprising a nucleic acid sequence encoding a 3' portion of an intron, the recognition sequence for the type IIs restriction endonuclease shall be followed by the cleavage sequence for said type IIs restriction endonuclease.

In an embodiment, the cleavage sequences comprised by the polynucleotides as referred to herein, i.e. by the first, second, third etc. polynucleotides are part of the 5' or 3' portion of the introns (to be ligated). E.g., the nucleic acid sequence encoding the 5' portion of the first intron in the first polynucleotide comprises the first cleavage sequence for a type IIs restriction endonuclease. E.g., the nucleic acid sequence encoding the 3' portion of the first intron in the second polynucleotide comprises the second cleavage sequence for a type IIs restriction endonuclease. After ligation, the resulting intron comprises the 5' portion of the intron, the cleavage site and the 3' portion of the intron (herein also referred to a functional intron). The recognition sequences are no longer present.

The cleavage sequence may be a sequence which occurs naturally in the introns as set forth herein. Alternatively, it may not occur naturally in the introns. In this case, it may have been added to the intron (e.g. by insertion), or it may have been generated by introducing point mutations into the sequence of a naturally occurring intron.

A large number of type IIs restriction endonucleases is commercially available. In an embodiment, the type IIs restriction endonuclease is selected from AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, and SfaNI. Preferably, the type IIs restriction endonuclease is selected from the group consisting of: BsaI, BbsI, FokI, BsmBI, BtgZI and SapI.

The second polynucleotide shall comprise a second cleavage sequence which is complementary to first cleavage sequence. In accordance with the present invention, the phrase that "a cleavage sequence which is complementary to another cleavage sequence" (such a second cleavage sequence which is complementary the first cleavage sequence), preferably, means that the overhangs created by cleavage with the endonuclease are complementary to each other, i.e. compatible.

In an embodiment of the present invention, only one type IIs restriction endonuclease is used. Said endonuclease recognizes all recognition sequences comprised by the polynucleotides to be assembled (the first, second etc. polynucleotide). In an alternative embodiment of the present invention, different type IIs restriction endonucleases having different recognition sites are used, e.g. two, three or more different type IIs restriction endonucleases. Said different endonuclease shall create overhangs which ideally have the same length (e.g. 4 nt) and complementary sequences in order to allow for ligating the cleaved polynucleotides.

Further, it is envisaged that the polynucleotides to be assembled do not comprise further recognition sequences for the type IIs restriction endonuclease to be used, i.e. they shall not comprise recognition sequence in addition to the recognition sequences as referred to herein in order to prevent cleavage at undesired positions. This is taken into account by the skilled person.

In step (b) of the aforementioned method of the present invention, the polynucleotides provided in step (a) are contacted with the type IIs restriction endonuclease and a ligase under conditions that allow for the cleavage of the first polynucleotide and second polynucleotide by said type IIs restriction endonuclease and the ligation of the resulting cleavage products, thereby producing the fusion polynucleotide encoding the polypeptide of interest.

The term "ligase" as used herein shall relate to an enzyme that is used to join polynucleotides together. The ligase to be applied in accordance with the method of the present invention shall be a DNA ligase. DNA ligases are well known in the art and include bacteriophage ligases such as T4 DNA Ligase, T7 DNA ligase, bacterial archeabacterial ligases. In preferred embodiment, the ligase is a T4 DNA ligase. This ligase requires ATP as a cofactor. By using the ligase, the polynucleotides that are provided in step (a) of the method of the present invention are ligated after cleavage with the endonuclease via the created complementary overhangs. Thereby, the polynucleotides are assembled in a directional manner.

The cleavage and ligation in step (b), i.e. the assembly of the polynucleotides, are carried out simultaneously or essentially simultaneously. Thus, the assembly is carried out in the presence of both a ligase and a type IIs restriction endonuclease. Both enzymes should be active. This kind of assembly is known as "Golden Gate" assembly.

Because the enzymes used for the assembly in step (b) have different temperature optima, the assembly is typically carried out in a thermocycler. A typical thermocycler protocol oscillates between about 37° C. (optimal for type IIs restriction endonuclease) and about 16° C. (optimal for ligases). Several cycles can be made. In a last step, the enzymes are inactivated by heat (e.g. at 65° C.). Programmable thermocyclers are readily available from a number of commercial suppliers.

After the cleavage and ligation, the products of the assembly are transformed into competent bacterial cells, such as E. coli cells.

The fusion polynucleotide encodes for a polypeptide of interest. It is to be understood that the fusion polynucleotide has to be expressed in a eukaryotic cell because prokaryotic cells do not possess a splicing machinery. In order to express the polynucleotide, it is operably linked to one or more expression control sequences. Preferably, the expression control sequences are heterologous with respect to said polynucleotide.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Thus, the expression control sequence is preferably a promoter. Expression of a polynucleotide comprises transcription of the nucleic acid molecule, preferably, into a translatable mRNA. Additional regulatory elements may include transcriptional as well as translational enhancers.

Preferably, the promotor shall be active in the eukaryotic host cells, more preferably in mammalian cells and/or insect cells. In an embodiment, the fusion polynucleotide is operably linked to a promoter selected from the CMV-5-, SV40-, RSV-, EF1a-, MPSV-, and SR alpha-promoter. For insect cells the polyhedron promoter, p10 promotor, or ie1 promoter may be used.

In order to allow for the expression, the fusion polynucleotide may be present in a vector. Preferably, the vector is a recombinant DNA construct suitable for expression of the fusion polynucleotide produced by the methods of the present invention. Moreover, the term also relates to targeting constructs which allow for random or site-directed integration of the targeting construct into genomic DNA. Such target constructs, preferably, comprise DNA of sufficient length for either homologous or heterologous recombination. The vector may comprise selectable markers for propagation and/or selection in a host.

A host cell in which the fusion polynucleotide shall be expressed may be any eukaryotic cell such as a mammalian (e.g. a human or mouse) cell, plant cell or insect cell. Preferably, the host cell is a eukaryotic cell, more preferably, a mammalian or insect cell. For example, the host cell may be a HEK-293 cell (human embryonic kidney cell 293) such as a HEK293E cell, a HEK-293T cell, or a Freestyle™ HEK-293 cell. Alternatively, the host cell may be a CHO cell (Chinese Hamster Ovary) such as a CHO-K1 cell.

The method of the present invention may be applied for producing a fusion polynucleotide encoding a pre-defined polypeptide of interest.

However, the method may also be applied for producing a plurality of different fusion polynucleotides encoding polypeptides of interest which differ in the order of the polypeptide portions encoded by the first, second and further polynucleotides used for generating the fusion polynucleotides. In such a case, the fusion polynucleotides, typically, comprise a first, a second, and at least one more polynucleotide as specified in accordance with the method of the present invention. However, it is envisaged for said application that the cleavage sequences for the type IIs restriction endonucleases in such a case between the further polynucleotides and/or the first and second polynucleotide are all complementary to each other such that the ligation of first, second and further polynucleotides occurs in a substantially random manner.

The term "polypeptide" is well understood by the skilled person. A polypeptide is a molecule composed of amino acid residues linearly linked by amide bonds (also known as peptide bonds). The polypeptide of interest may have any length. For example, the polypeptide of interest may be a polypeptide comprising at least 50, 100, 300, or 500 amino acids. Depending on construct, the polypeptide may be even longer, for example if the polypeptide of interest to be generated is an artificial antibody. E.g., the polypeptide of interest may comprise at least 2000 amino acids.

Figure 2:
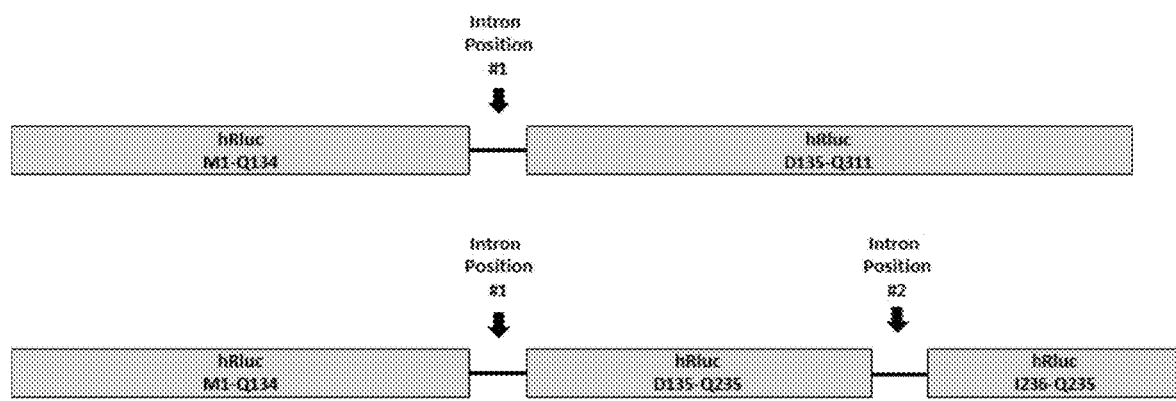
FIG. 2: Luciferase experiments with one or two introns: Intron positions in Renilla Luciferase Gene. Boxes depict "exons", the black horizontal bars represent artificially inserted introns.
Figure 3:
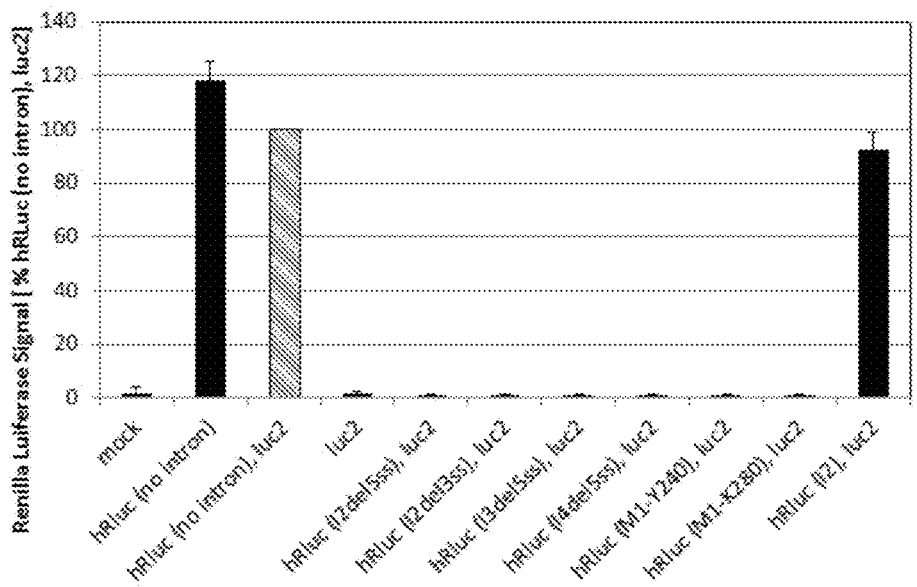
FIG. 3: hRluc expression—Mutation of canonical splice sites in introns #2 & #3 destroys expression of Renilla luciferase as does the deletion of parts of its C-terminal sequence. The x-axis depicts the constructs with or without introns in the hRluc gene. The y-axis shows the expression level of each construct relative to the reference construct without intron (hatched bar). Constructs shown comprise those with (non-)functional introns at intron position #1 (see FIG. 2) and C-terminal deletion constructs of hRluc. Error bars: standard deviation.
Figure 4:
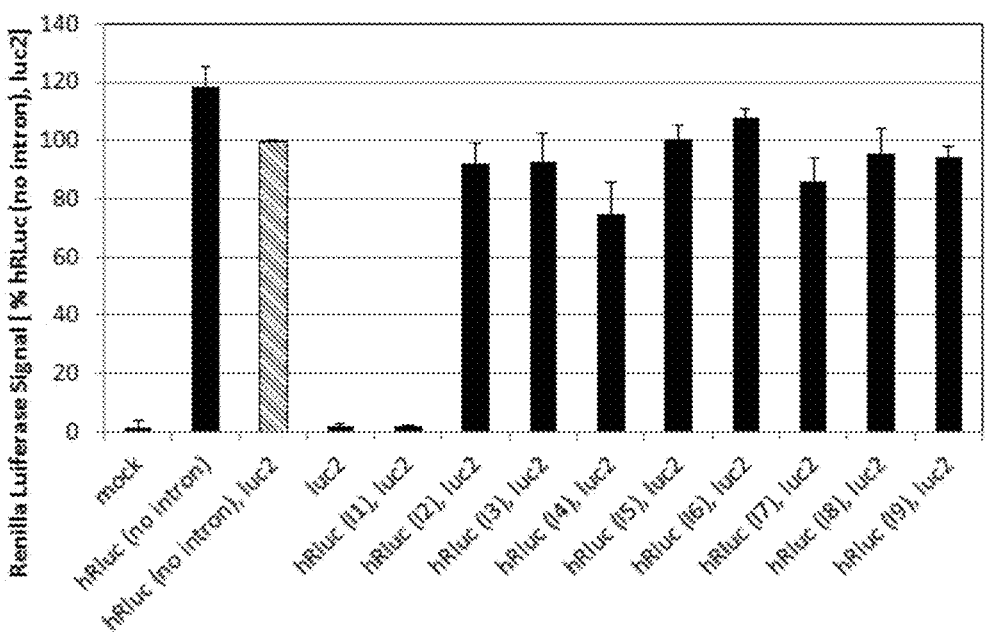
FIG. 4: hRluc expression—Constructs with a single intron at intron position #1 of hRluc retain the expression level of the intron-less control construct. Only intron #1 does not lead to functional expression of protein. Reference construct: hatched bar. Error bars: standard deviation. For usage of x- and y-axes, see FIG. 3.
Figure 5:
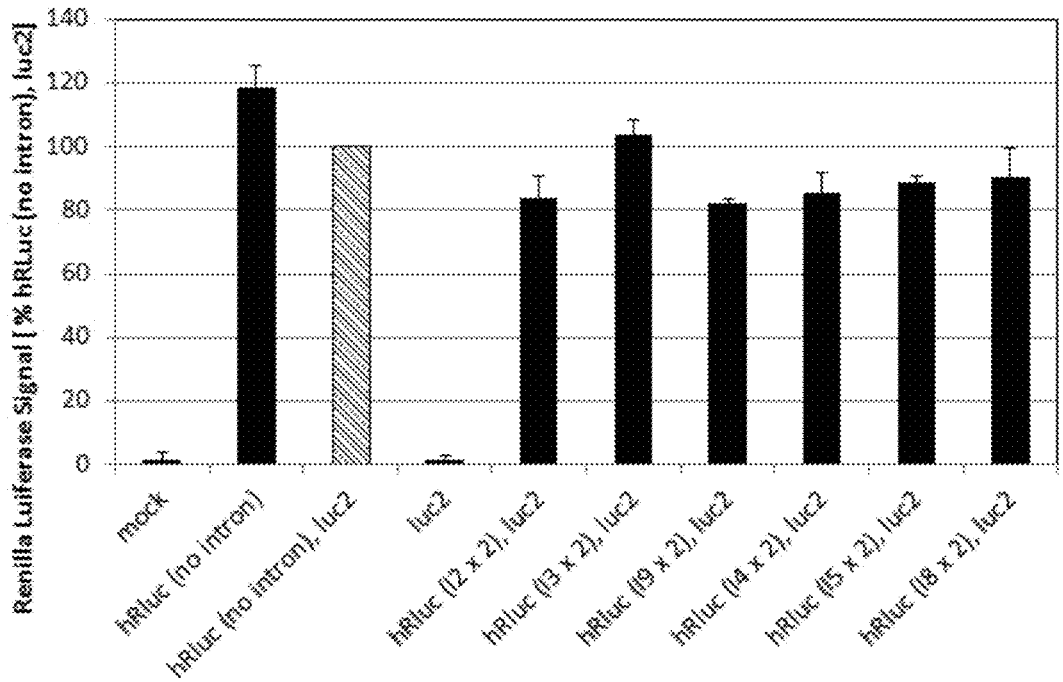
FIG. 5: hRluc expression—Constructs with two identical introns at intron positions #1 & #2 of hRluc retain at least 80% of the expression level of the intronless control construct. Reference construct: hatched bar. Error bars: standard deviation. For usage of x- and y-axes, see FIG. 3.
Figure 6:
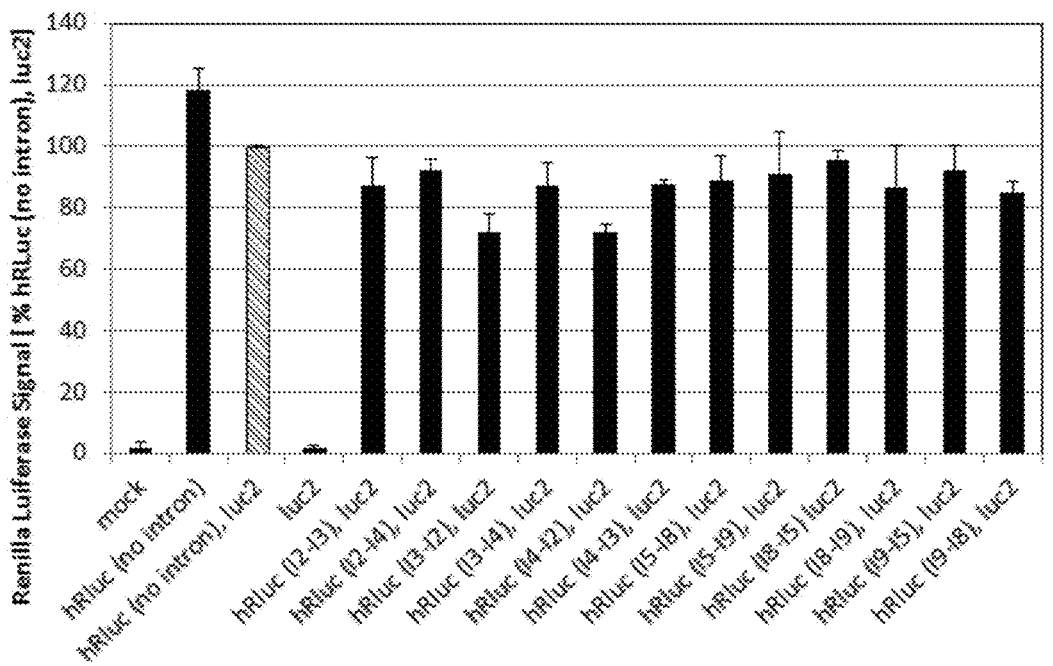
FIG. 6: hRluc expression—Constructs with two different introns at intron positions #1 & #2 of hRluc retain at least 70% of the expression level of the intronless control construct—in whatever combination is used. Reference construct: hatched bar. Error bars: standard deviation. For usage of x- and y-axes, see FIG. 3.
Figure 7:
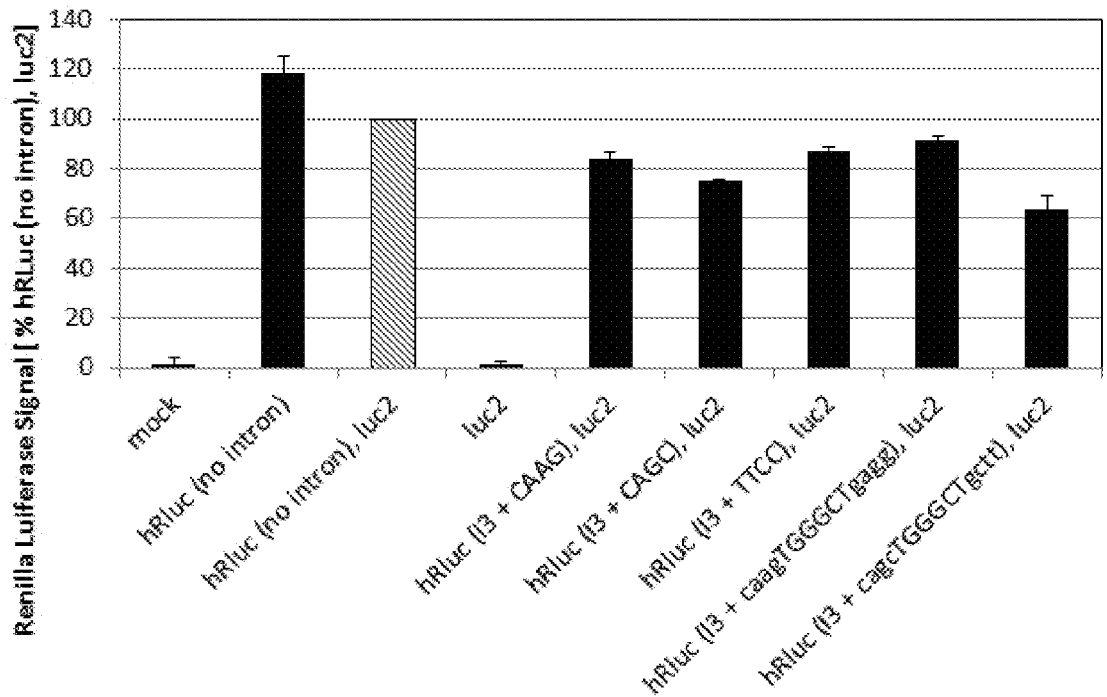
FIG. 7: hRluc expression—Constructs with various modifications of intron 13 at intron position #1 of hRluc show between 60-90% of the intron-less control construct—depending more on the type of the inserted sequence than on its length. Reference construct: hatched bar. Error bars: standard deviation. For usage of x- and y-axes, see FIG. 3. Sequences in the figure: caagtgggctgag is SEQ ID NO: 41, cagctgggctgctt is SEQ ID NO: 42.
Figure 8:
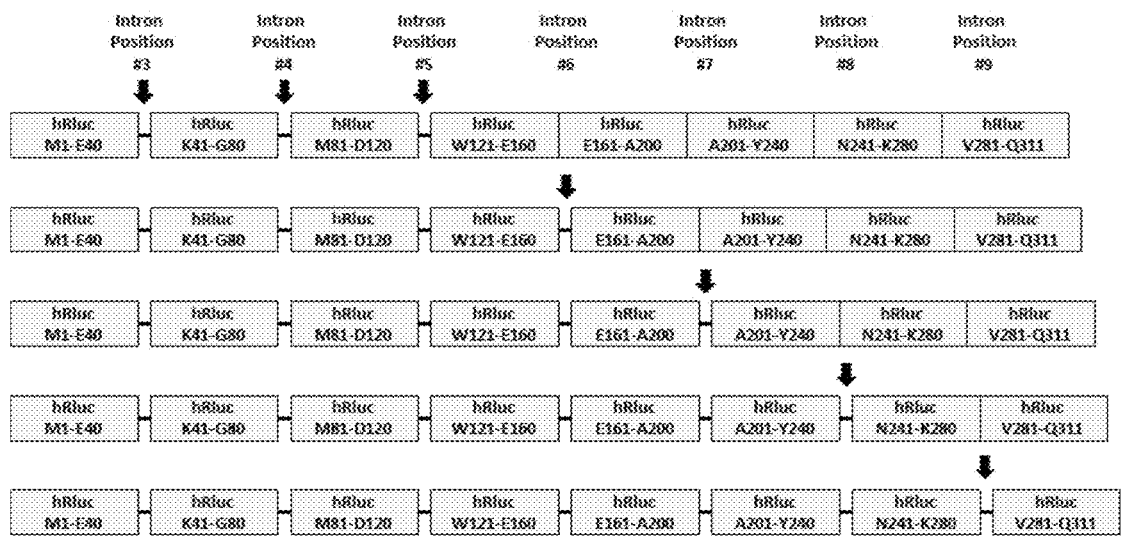
FIG. 8: Luciferase experiments with three to seven introns: Intron positions in Renilla Luciferase Gene. Boxes depict "exons", the black horizontal bars represent introns. Constructs with more than three introns all contain introns at positions #3, #4, and #5.
Figure 9:
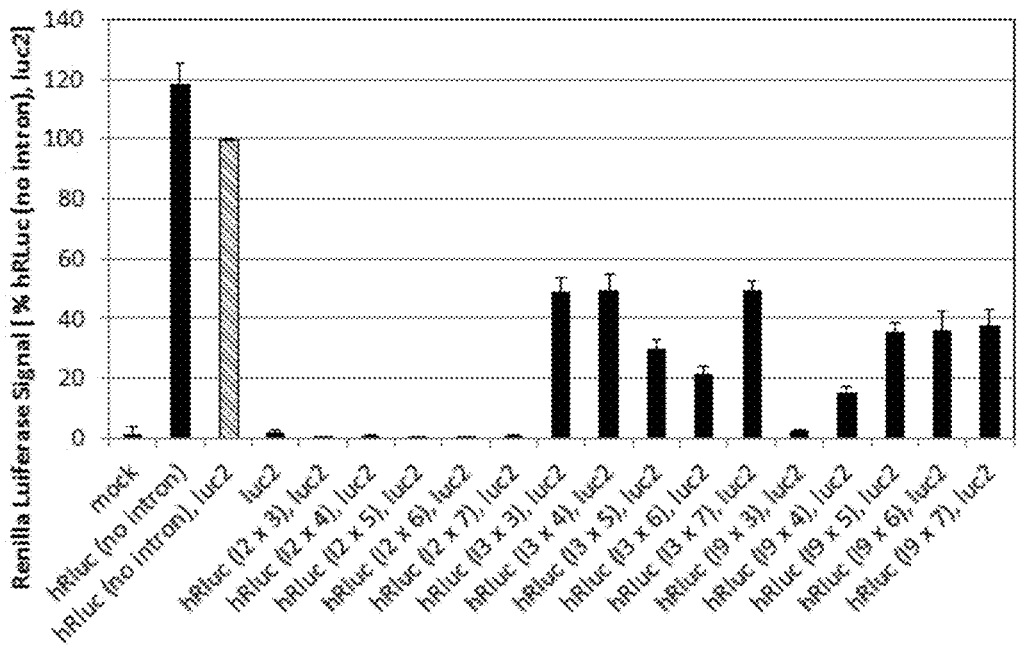
FIG. 9: hRluc expression—Constructs with 3 to 7 identical introns at intron positions #3-#7 (see FIG. 8) of hRluc show reduced levels of expression as compared to the control construct without intron. The number of introns used per construct does not seem to have the same effect in all constructs. Intron #2 does not seem to work if more than two copies are used in the same construct. Reference construct: hatched bar. Error bars: standard deviation. For usage of x- and y-axes, see FIG. 3.
Figure 10:
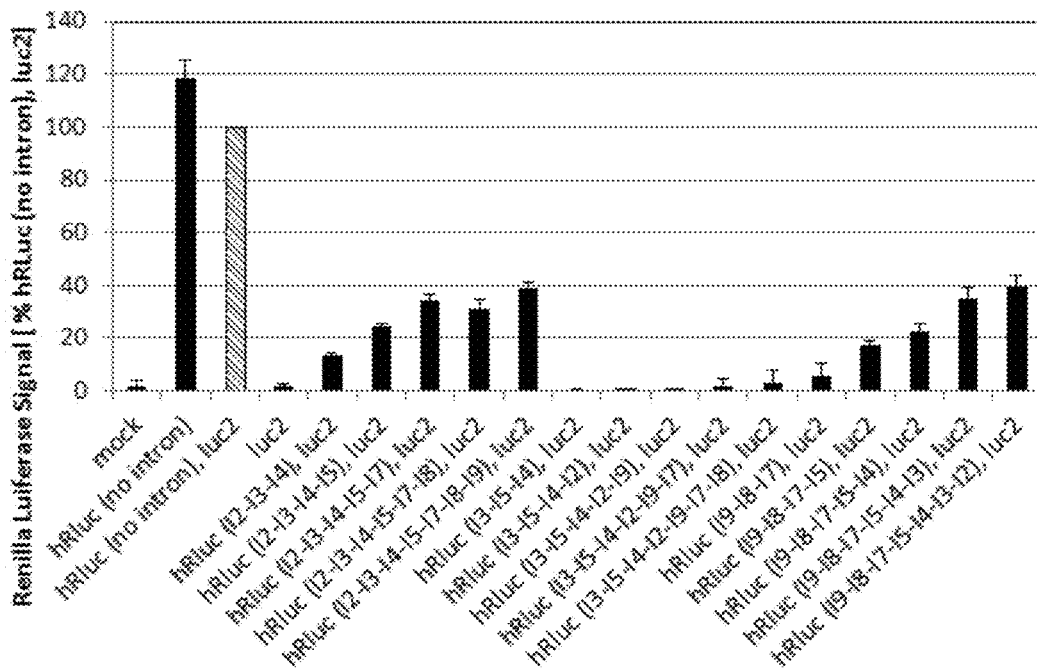
FIG. 10: hRluc expression—Constructs with 3 to 7 different introns at intron positions #3-#7 of hRluc show reduced levels of expression when compared to the control construct without intron. Here it seems as if there is trend that more introns increase the expression level. Expression seems to be dependent on the combination of introns used and the order in which they are used. Reference construct: hatched bar. Error bars: standard deviation. For usage of x- and y-axes, see FIG. 3.
Figure 11A:
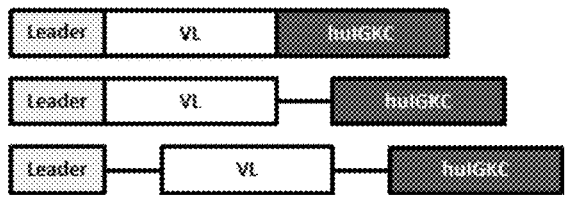
FIGS. 11A and 11B: Antibody constructs (light chain and heavy chain) with one or two introns between the variable domain and the constant domain (one intron, see Figure 11A)), or both between the leader sequence and the variable domain and the variable domain and the constant domain (two introns, see FIG. 11B)).
Figure 11B:
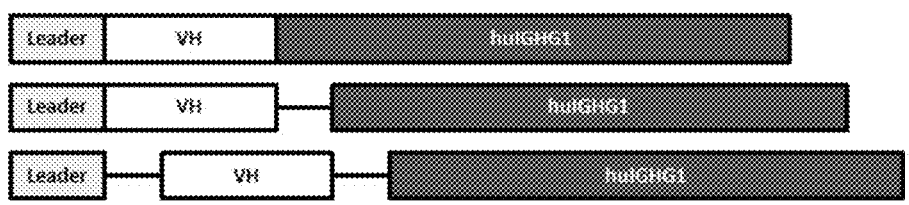
Figure 12:
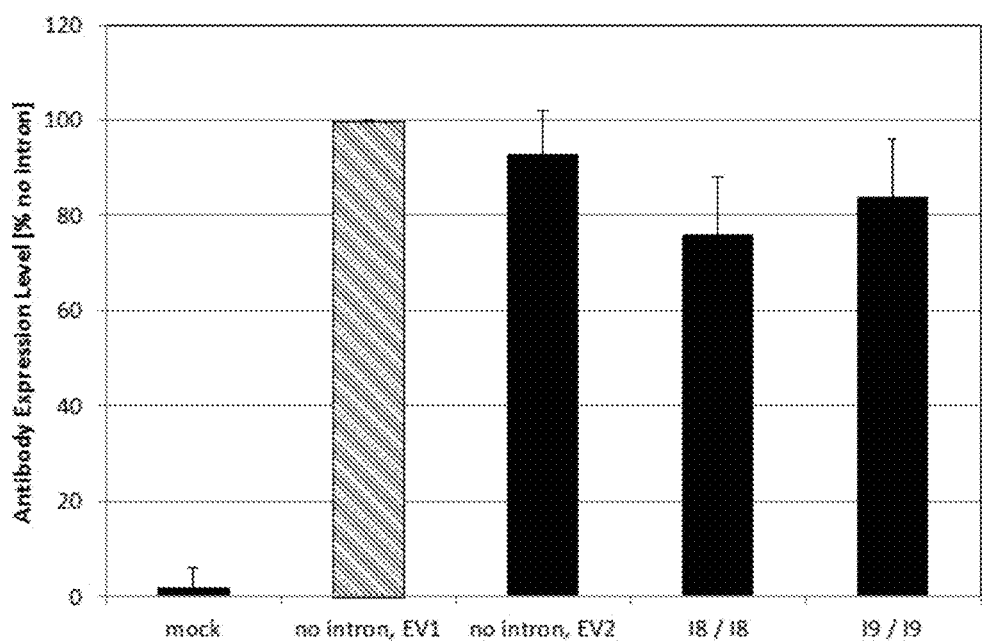
FIG. 12: Antibody Expression—Expression levels of antibodies produced from sequences with or without introns are comparable. The x-axis depicts the constructs with or without introns in the antibody's light and heavy chain gene. The y-axis shows the expression level of each construct relative to the reference construct without intron (hatched bar). Constructs shown comprise antibodies containing no intron or one intron per chain either in slightly different expression vectors (EV1 & EV2) or in expression vector EV2 (18/18, 19/19)—see FIGS. 11A and 11B for intron positions. Error bars: standard deviation from 12 independent experiments.
Figure 13:
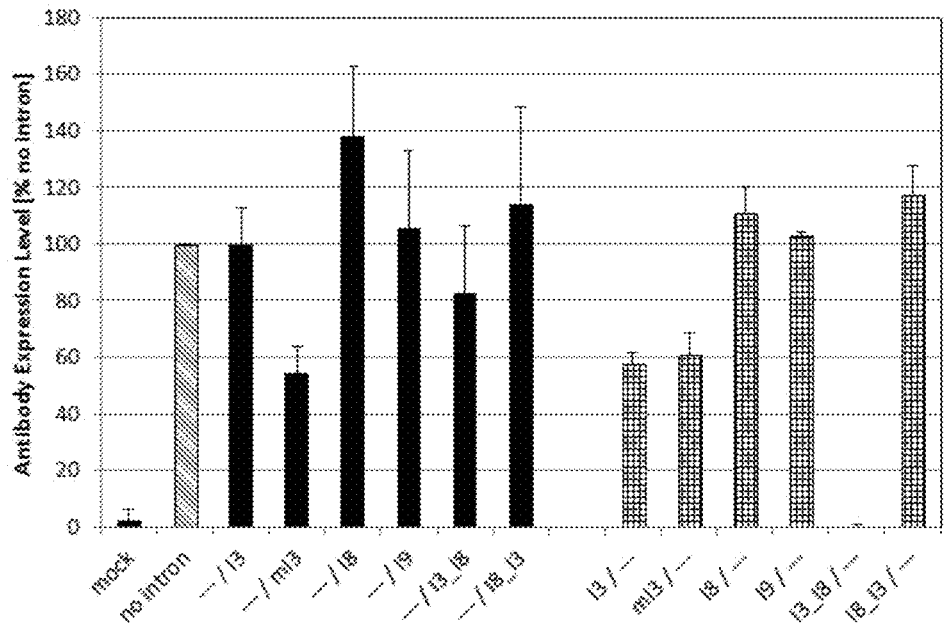
FIG. 13: Antibody Expression—Comparison of constructs containing one intron in either the heavy chain (black bars) or the light chain (chequered bars) often show lower expression for those constructs containing intron #3 or a modified form of intron #3 (m13). The light chain seems to be more strongly affected. In contrast, intron #8 or #9 are expressed at either the same level as the control or show even elevated expression levels. Reference construct: hatched bar. Construct names contain the intron references in the order light chain/heavy chain: "---" depicts a light or heavy chain without intron, all others contain an original intron (13, 18, 19) or a hybrid intron (13_18, 18_13). The x-axis depicts the constructs with or without introns in the antibody's light or heavy chain gene. The y-axis shows the expression level of each construct relative to the reference construct without intron (hatched bar). Error bars: standard deviation from three independent experiments, 12 experiments for the mock and no-intron control.
Figure 14:
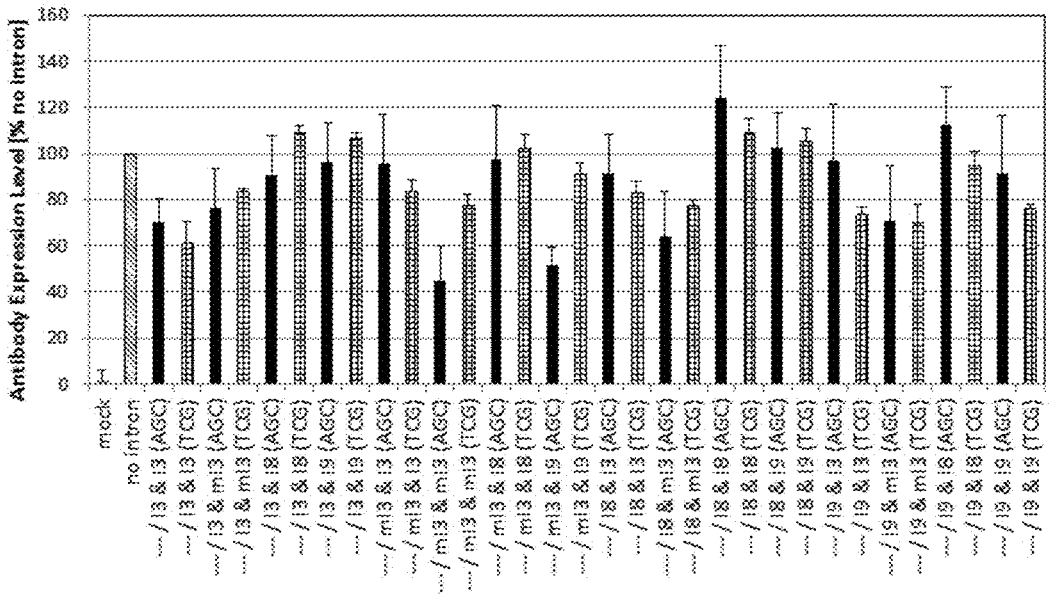
FIG. 14: Antibody Expression—Usage of different terminal codons at the 3' end of the leader sequence: usage of AGC (black bars) or TCG (chequered bars) does not influence the expression levels of various constructs containing two introns in the heavy chain sequence. Thus, the least often used nucleotide "C" at position −1 relative to the intron start, does not diminish expression when compared to "G" which represents the most often used last nucleotide in exons. Usage of intron combinations containing neither wild type intron #3 or a modified version of it (m13) show more stable expression levels when compared to the control construct. Reference construct: hatched bar. Construct names contain the intron references in the order light chain ("---"=no intron)/heavy chain. The x-axis depicts the constructs with or without introns in the antibody's light or heavy chain gene. The y-axis shows the expression level of each construct relative to the reference construct without intron (hatched bar). Error bars: standard deviation from three independent experiments, 12 experiments for the mock and no-intron control.
Figure 15:
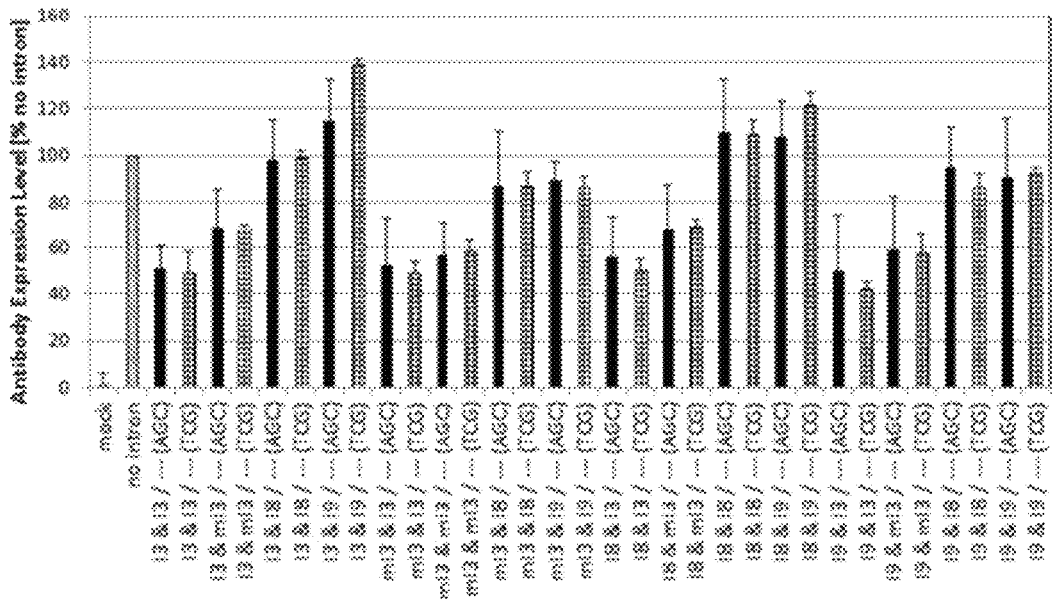
FIG. 15: Antibody Expression—Usage of different terminal codons at the 3' end of the leader sequence: usage of AGC (black bars) or TCG (chequered bars) does not influence the expression levels of various constructs containing two introns in the light chain sequence. Thus, the least often used nucleotide "C" at position −1 relative to the intron start, does not diminish expression when compared to "G" which represents the most often used last nucleotide in exons. Usage of intron combinations containing neither wild type intron #3 or a modified version of it (m13) show more stable expression levels when compared to the control construct. Reference construct: hatched bar. Construct names contain the intron references in the order light chain/heavy chain ("---"=no intron). The x-axis depicts the constructs with or without introns in the antibody's light or heavy chain gene. The y-axis shows the expression level of each construct relative to the reference construct without intron (hatched bar). Error bars: standard deviation from three independent experiments, 12 experiments for the mock and no-intron control.
Figure 16:
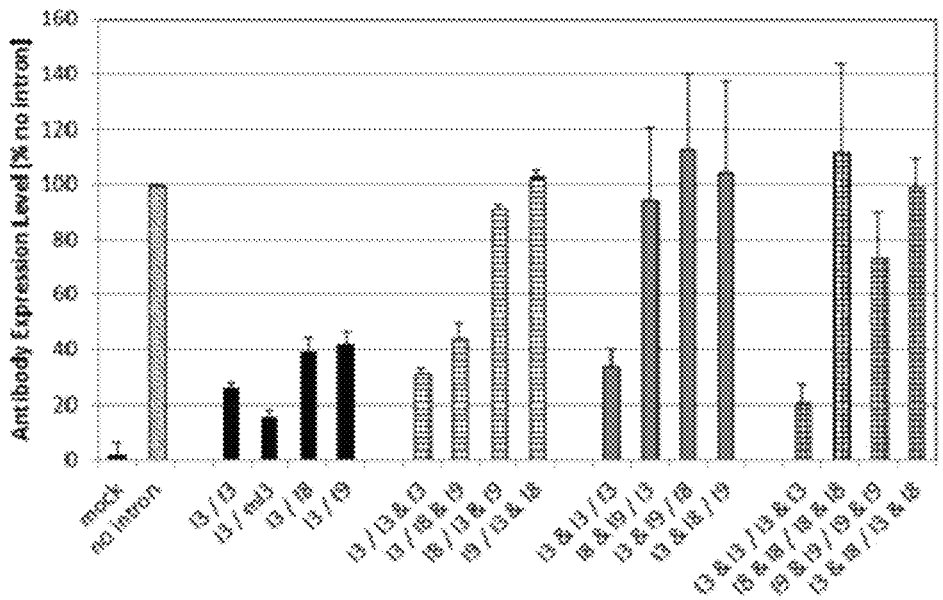
FIG. 16: Antibody Expression—Various intron combinations in both light and heavy chains almost always show a negative influence of intron #3 on the expression level when no other intron is present on the same chain. Expression levels can increase again when intron #3 is combined with intron #8 or #9 on the same chain. Black bars: one intron in each chain, striped bars: one intron in the light chain, two introns in the heavy chain, gray bars: two introns in the light chain, one intron in the heavy chain, chequered bars: two introns in each chain). Reference construct: hatched bar. Construct names contain the intron references in the order light chain/heavy chain. The x-axis depicts the constructs with various introns or intron combinations in the antibody's light or heavy chain gene ("m13"=modified version of intron #3). The y-axis shows the expression level of each construct relative to the reference construct without intron (hatched bar). Error bars: standard deviation from three independent experiments, 12 experiments for the mock and no-intron control.

In the studies underlying the present invention, different fusion polypeptides were analysed (a luciferase and an antibody, see FIGS. 1 to 16). The present invention however is not limited to these polypeptides. In principle, the polypeptide of interest can be any polypeptide. For example, in certain embodiments the polypeptide of interest is a naturally occurring polypeptide. Typically, said polypeptide is an enzyme, a transcription factor, a nuclease, a ligand protein, a therapeutic protein, a transcription factor, a growth factor, a growth factor receptor. Also, the polypeptide of interest may be an antibody or a derivative thereof, e.g. bispecific or multispecific protein constructs/antibodies. In certain embodiments, the polypeptide of interest is a fusion protein comprising parts or all of at least two naturally occurring polypeptides. In certain embodiments, the polypeptide of interest is a fusion protein comprising parts or all of at least one naturally occurring polypeptide and at least one non-naturally occurring polypeptide. For example, the polypeptide of interest may be a fusion of a therapeutic peptide or protein and a therapeutic antibody, or antigen-binding fragment thereof.

As set forth above, said polypeptide of interest may be an also antibody, or an antigen binding fragment thereof. An antibody may also be a bispecific antibody or multispecific antibody. The term "bispecific antibody" as used herein refers to an antibody that specifically binds to two different epitopes. A multispecific antibody is an antibody which binds to two or more different epitopes. The different epitopes of said bispecific and multispecific antibody are typically non-overlapping epitopes. Further, the antibody may a bivalent or multivalent antibody. In an embodiment, the antibody is a multispecific, multivalent antibody. In an embodiment, the antibody is a bispecific, bivalent antibody.

In an embodiment, the polypeptide of interest is a non-naturally occurring polypeptide.

The method of the present invention allows not only for the assembly of two polynucleotides but also for the assembly of three or more polynucleotides. For example, three, four, five, six, seven, eight, nine or ten polynucleotides can be assembled, i.e. ligated, in a predetermined order to produce a fusion polynucleotide that encodes for the polypeptide of interest. If more than two polynucleotides are assembled to produce the fusion polynucleotide, the polynucleotides to be assembled that will be located at a central position (herein also referred to as central polynucleotides) of the fusion polynucleotide comprise cleavage and recognition sites for the type IIs restriction endonuclease at both ends, i.e. at the 5' end and the 3' end. The polynucleotides to be assembled that will be at the ends of the fusion polynucleotide (herein also referred to as terminal polynucleotides) might comprise only at one end a cleavage and recognition site for the type IIs restriction endonuclease. However, it is also envisaged that said terminal polynucleotides comprise at both ends a cleavage and recognition site for the type IIs restriction endonuclease. This would e.g. allow the cloning of the polynucleotide encoding the polypeptide of interest into a vector (such as an expression vector). As described herein elsewhere the cleavage site and the recognition site shall be operably linked to each other.

In an embodiment of the method of the present invention, the method comprises the assembly, i.e. the ligation, of three polynucleotides: of the first polynucleotide as set forth above, the second polynucleotide as set forth above, and of a third polynucleotide. The polynucleotides which are provided in steps (a1), (a2) and (a3), respectively, shall be ligated in the following order (from 5' to 3'):

First polynucleotide (terminal polynucleotide)—second polynucleotide (central polynucleotide)—third polynucleotide (terminal polynucleotide).

Since the second polynucleotide becomes the central polynucleotide, it comprises in addition to the elements (i) to (iv) of the second polynucleotide as set forth in step (a2) of the method of the present invention the following sequences (again in 5' to 3' direction):

(v) a nucleic acid sequence encoding a 5' portion of a second intron,
(vi) a third cleavage sequence for the type IIs restriction endonuclease, which differs from the first cleavage sequence of the first polynucleotide, and
(vii) a recognition sequence for the type IIs restriction endonuclease, wherein the third cleavage sequence in (vi) is operably linked to said recognition sequence.

The method further comprises step (a3). Said step is carried out prior to step (b). In step (a3) of the method of the present invention, a third polynucleotide is provided, comprising, in 5' to 3' direction:

(i) a recognition sequence for the type IIs restriction endonuclease,
(ii) a fourth cleavage sequence for the type IIs restriction endonuclease, wherein said fourth cleavage sequence is complementary to the third cleavage sequence, wherein the fourth cleavage sequence in (ii) is operably linked to said recognition sequence, i.e. to the recognition sequence of the third polynucleotide under (i),
(iii) a nucleic acid sequence encoding a 3' portion of the second intron, and
(iv) a nucleic acid sequence encoding a third portion of the polypeptide of interest.

In an embodiment of the method of the present invention, the method comprises the assembly, i.e. the ligation, of four polynucleotides: of the first polynucleotide as set forth above, the second polynucleotide as set forth in connection with the assembly of three polynucleotides, and of the third polynucleotide as set forth above, and of a fourth polynucleotide. The polynucleotides which are provided in steps (a1), (a2), (a3) and (a4), respectively shall be ligated in the following order (from 5' to 3'):

First polynucleotide (terminal polynucleotide)—second polynucleotide (central polynucleotide)—third polynucleotide (central polynucleotide)—fourth polynucleotide (terminal polynucleotide)

Since the third polynucleotide becomes a central polynucleotide, it comprises in addition to the elements (i) to (iv) of the third polynucleotide as set forth in step (a3) above the following sequences (again in 5' to 3' direction):

(v) a nucleic acid sequence encoding a 5' portion of a third intron,
(vi) a fifth cleavage sequence for the type IIs restriction endonuclease, which differs from the first cleavage sequence of the first polynucleotide and the third cleavage sequence of the second polynucleotide, and
(vii) a recognition sequence for the type IIs restriction endonuclease, wherein the fifth cleavage sequence in (vi) is operably linked to said recognition sequence (i.e. the recognition sequence in (vii)).

The method further comprises step (a4). Said step is carried out prior to step (b). In step (a4) of the method of the present invention, a fourth polynucleotide is provided, comprising, in 5' to 3' direction:

(i) a recognition sequence for the type IIs restriction endonuclease,
(ii) a sixth cleavage sequence for the type IIs restriction endonuclease, wherein said sixth cleavage sequence is complementary to the fifth cleavage sequence, wherein the sixth cleavage sequence in (ii) is operably linked to said recognition sequence in (i),
(iii) a nucleic acid sequence encoding a 3' portion of the third intron, and
(iv) a nucleic acid sequence encoding a fourth portion of the polypeptide of interest.

In an embodiment of the method of the present invention, the method comprises the assembly, i.e. the ligation, of five polynucleotides: of the first polynucleotide as set forth above, the second polynucleotide as set forth in connection with the assembly of three polynucleotides, of the third polynucleotide in connection with the assembly of four polynucleotides, of a fourth polynucleotide as set forth above, and a fifth polynucleotide The polynucleotides which are provided in steps (a1), (a2), (a3), (a4) and (a5), respectively, shall be ligated in the following order (from 5' to 3'):

First polynucleotide (terminal polynucleotide)—second polynucleotide (central polynucleotide)—third polynucleotide (central polynucleotide)—fourth polynucleotide (central polynucleotide)—fifth polynucleotide (terminal polynucleotide)

Since the fourth polynucleotide becomes a central polynucleotide, it comprises in addition to the elements (i) to (iv) of the fourth polynucleotide as set forth in step (a4) above the following sequences (again in 5' to 3' direction):

(v) a nucleic acid sequence encoding a 5' portion of a fourth intron,
(vi) a seventh cleavage sequence for the type IIs restriction endonuclease, which differs from the first cleavage sequence of the first polynucleotide, the third cleavage sequence of the second polynucleotide, and the fifth cleavage sequence of the third polynucleotide, and
(vii) a recognition sequence for the type IIs restriction endonuclease, wherein said seventh cleavage sequence in (vi) is operably linked to said recognition sequence in (vii).

The method further comprises step (a5). Said step is carried out prior to step (b). In step (a5) of the method, a fifth polynucleotide is provided, comprising, in 5' to 3' direction:
- (i) a recognition sequence for the type IIs restriction endonuclease
- (ii) an eighth cleavage sequence for the type IIs restriction endonuclease, wherein said eighth cleavage sequence is complementary to the seventh cleavage sequence, wherein the cleavage sequence in (ii) is operably linked to the recognition sequence in (i),
- (iii) a nucleic acid sequence encoding a 3' portion of the fourth intron, and
- (iv) a nucleic acid sequence encoding a fifth portion of the polypeptide of interest.

In an embodiment of the method of the present invention, the method comprises the assembly, i.e. the ligation, of six polynucleotides: of the first polynucleotide as set forth above, the second polynucleotide as set forth in connection with the assembly of three polynucleotides, of the third polynucleotide as set forth in connection with the assembly of four polynucleotides, of a fourth polynucleotide as set forth in connection with the assembly of five polynucleotides, a fifth polynucleotide as set forth above, and a sixth polynucleotide The polynucleotides which are provided in steps (a1), (a2), (a3), (a4), (a5) and (a6), respectively, shall be ligated in the following order (from 5' to 3'):

First polynucleotide (terminal polynucleotide)—second polynucleotide (central polynucleotide)—third polynucleotide (central polynucleotide)—fourth polynucleotide (central polynucleotide)—fifth polynucleotide (central polynucleotide)—sixth polynucleotide (terminal polynucleotide)

Since the fifth polynucleotide becomes a central polynucleotide, it comprises in addition to the elements (i) to (iv) of the fifth polynucleotide as set forth in step (a5) above the following sequences (again in 5' to 3' direction):
- (v) a nucleic acid sequence encoding a 5' portion of a fifth intron,
- (vi) a ninth cleavage sequence for the type IIs restriction endonuclease, which differs from the first cleavage sequence of the first polynucleotide, the third cleavage sequence of the second polynucleotide, the fifth cleavage sequence of the third polynucleotide, and the seventh cleavage sequence of the fourth polynucleotide, and
- (vii) a recognition sequence for the type IIs restriction endonuclease, wherein the ninth cleavage sequence in (vi) is operably linked to the recognition sequence in (vii).

The method further comprises step (a6). Said step is carried out prior to step (b). In step (a6) of the method, a sixth polynucleotide is provided, comprising, in 5' to 3' direction:
- (i) a recognition sequence for the type IIs restriction endonuclease,
- (ii) a tenth cleavage sequence for the type IIs restriction endonuclease, wherein said tenth cleavage sequence is complementary to the ninth cleavage sequence, wherein the tenth cleavage sequence in (ii) is operably linked to the recognition sequence in (i),
- (iii) a nucleic acid sequence encoding a 3' portion of the fifth intron, and
- (iv) a nucleic acid sequence encoding a sixth portion of the polypeptide of interest.

In an embodiment of the method of the present invention, the method comprises the assembly, i.e. the ligation, of seven polynucleotides: of the first polynucleotide as set forth above, the second polynucleotide as set forth in connection with the assembly of three polynucleotides, of the third polynucleotide as set forth in connection with the assembly of three polynucleotides, of a fourth polynucleotide as set forth in connection with the assembly of five polynucleotides, a fifth polynucleotide as set forth in connection with the assembly of six polynucleotides, a sixth polynucleotide as set forth above, and a seventh polynucleotide. The polynucleotides which are provided in steps (a1), (a2), (a3), (a4), (a5), (a6) and (a7), respectively, shall be ligated in the following order (from 5' to 3'):

First polynucleotide (terminal polynucleotide)—second polynucleotide (central polynucleotide)—third polynucleotide (central polynucleotide)—fourth polynucleotide (central polynucleotide)—fifth polynucleotide (central polynucleotide)—sixth polynucleotide (central polynucleotide)—seventh polynucleotide (terminal polynucleotide)

Since the sixth polynucleotide becomes a central polynucleotide, it comprises in addition to the elements (i) to (iv) of the sixth polynucleotide as set forth in step (a6) above the following sequences (again in 5' to 3' direction):
- (v) a nucleic acid sequence encoding a 5' portion of a sixth intron,
- (vi) an eleventh cleavage sequence for the type IIs restriction endonuclease, which differs from the first cleavage sequence of the first polynucleotide, the third cleavage sequence of the second polynucleotide, the fifth cleavage sequence of the third polynucleotide, the seventh cleavage sequence of the fourth polynucleotide, and the ninth cleavage sequence of the fifth polynucleotide, and
- (vii) a recognition sequence for the type IIs restriction endonuclease, wherein the eleventh cleavage sequence in (vi) is operably linked to the recognition sequence in (vii).

The method further comprises step (a7). Said step is carried out prior to step (b). In step (a7) of the method, a seventh polynucleotide is provided, comprising, in 5' to 3' direction: (i) a recognition sequence for the type IIs restriction endonuclease,
- (ii) a twelfth cleavage sequence for the type IIs restriction endonuclease, wherein said cleavage sequence is complementary to the eleventh cleavage sequence, wherein the twelfth cleavage sequence in (ii) is operably linked to the recognition sequence in (i),
- (iii) a nucleic acid sequence encoding a 3' portion of the sixth intron, and
- (iv) a nucleic acid sequence encoding a seventh portion of the polypeptide of interest.

The assembly, and thus the ligation, of the three, four, five, six, seven etc. polynucleotides as defined above takes place in step (b) of the method of the present invention.

In this step (b), the three, four, five, six, or seven etc. polynucleotides as defined above are contacted with the type IIs restriction endonuclease and a ligase under conditions that a1-low for the cleavage of the said polynucleotides by said type IIs restriction endonuclease and the ligation of the resulting cleavage products, thereby producing the fusion polynucleotide encoding the polypeptide of interest.

If three polynucleotides are provided and ligated, the fusion polynucleotide comprises, in 5' to 3' direction,
- (aa) the nucleic acid sequence encoding the first portion of the polypeptide of interest,
- (bb) a nucleic acid sequence encoding a first intron, wherein said first intron is functional, and wherein said first intron comprises the nucleic acid sequence encoding the 5' portion of the first intron and the nucleic acid sequence encoding the 3' portion of the first intron, (cc) the nucleic acid sequence encoding the second portion of the polypeptide of interest,
(dd) a nucleic acid sequence encoding a second intron, wherein said second intron is functional, and wherein said second intron comprises the nucleic acid sequence encoding the 5' portion of the second intron and the nucleic acid sequence encoding the 3' portion of the second intron, and
(ee) the nucleic acid sequence encoding the third portion of the polypeptide of interest.

If four polynucleotides are provided and ligated, the fusion polynucleotide further comprises, in 5' to 3' direction:
(ff) a nucleic acid sequence encoding a third intron, wherein said third intron is functional, and wherein said third intron comprises the nucleic acid sequence encoding the 5' portion of the third intron and the nucleic acid sequence encoding the 3' portion of the third intron, and
(gg) the nucleic acid sequence encoding the fourth portion of the polypeptide of interest.

If five polynucleotides are provided, the fusion polynucleotide further comprises, in 5' to 3' direction:
(hh) a nucleic acid sequence encoding a fourth intron, wherein said fourth intron is functional, and wherein said fourth intron comprises the nucleic acid sequence encoding the 5' portion of the fourth intron and the nucleic acid sequence encoding the 3' portion of the fourth intron,
(ii) the nucleic acid sequence encoding the fifth portion of the polypeptide of interest.

If six polynucleotides are provided, the fusion polynucleotide further comprises, in 5' to 3' direction:
(jj) a nucleic acid sequence encoding a fifth intron, wherein said fifth intron is functional, and wherein said fourth intron comprises the nucleic acid sequence encoding the 5' portion of the fifth intron and the nucleic acid sequence encoding the 3' portion of the fifth intron,
(kk) the nucleic acid sequence encoding the sixth portion of the polypeptide of interest.

If seven polynucleotides are provided, the fusion polynucleotide further comprises, in 5' to 3' direction:
(ll) a nucleic acid sequence encoding a sixth intron, wherein said sixth intron is functional, and wherein said sixth intron comprises the nucleic acid sequence encoding the 5' portion of the sixth intron and the nucleic acid sequence encoding the 3' portion of the sixth intron,
(mm) the nucleic acid sequence encoding the seventh portion of the polypeptide of interest.

The produced fusion polynucleotide as set forth above, when transcribed in a eukaryotic host cell, is transcribed into a transcript that is processed in said cell so that the introns which are functional are spliced out of said transcript, thereby producing an mRNA encoding the polypeptide of interest.

In a first embodiment, all introns transcribed by the transcript are identical or essentially identical. Thus, the first intron, the second intron, and the third intron etc. are identical or essentially identical. Surprisingly, it was shown in the studies underlying the present invention that identical introns can be used at multiple positions within a construct without hampering the expression of the protein of interest in many cases (see Examples). Polynucleotides with identical or essentially identical introns can be generated by shifting the cleavage site within the intron, i.e. by using 5' and 3' portions of the same intron which differ in their length. Thus, the 5' and 3' portions for the first intron differ in length from the 5' and 3' portions for the second intron. Ligation of the different portions will result in two identical or essentially identical introns.

In a second embodiment, all introns differ from each other. Thus, different introns are used. In this case, a unique cleavage site is used for the assembly of each intron. Further, it is possible to generate constructs with different introns by using a single intron with different cleavage sites. Such cleavage sites may have been introduced into the intron.

In a third embodiment, the transcript may comprise introns which are identical to other introns in the transcript, and further at least one intron which differs from the remaining introns. Thus, the transcript may comprise introns which occur more than once and one or more other introns differing from these introns. Said one or more other introns can be identical or non-identical to one another.

The present invention further allows the assembly of more than seven polynucleotides. In general, step (a) and (b) of the method of the present invention are as follows:

(a) providing n polynucleotides, n being an integer of at least 3,
  wherein the polynucleotide numbered 1, comprises in, in 5' to 3' direction,
    (i) a nucleic acid sequence encoding a portion, numbered 1, of the polypeptide of interest,
    (ii) a nucleic acid sequence encoding a 5' portion of an intron numbered 1,
    (iii) a cleavage sequence, numbered 1, for a type IIs restriction endonuclease, and
    (iv) a recognition sequence for said type IIs restriction endonuclease,
  wherein the cleavage sequence in (iii) is operably linked to the recognition sequence in (iv),
  wherein the polynucleotide(s) numbered 2 to (n−1), comprise(s), in 5' to 3' direction,
    (i) a recognition sequence for the type IIs restriction endonuclease
    (ii) a cleavage sequence for the type IIs restriction endonuclease, wherein said cleavage sequence is complementary to the cleavage sequence numbered 1 to (n−2), wherein the cleavage sequence in (ii) is operably linked to the recognition sequence in (i),
    (iii) a nucleic acid sequence encoding a 3' portion of the intron numbered 1 to (n−2), and
    (iv) a nucleic acid sequence encoding a portion, numbered 2 to (n−1), of the polypeptide of interest,
    (v) a nucleic acid sequence encoding a 5' portion of an intron numbered 2 to (n−1),
    (vi) a cleavage sequence, numbered 2 to (n−1), for the type IIs restriction endonuclease, which differs from the cleavage sequence(s) having a different number, and
    (vii) a recognition sequence for the type IIs restriction endonuclease, wherein the cleavage sequence in (vi) is operably linked to the recognition sequence in (vii).
  wherein the polynucleotide numbered n, comprise(s), in 5' to 3' direction,
    (i) a recognition sequence for the type IIs restriction endonuclease
    (ii) a cleavage sequence, for the type IIs restriction endonuclease, wherein said cleavage sequence is complementary to cleavage sequence, numbered n−1, wherein the cleavage sequence in (ii) is operably linked to the recognition sequence in (i), (iii) a nucleic acid sequence encoding a 3' portion of the intron, numbered (n−1), and
(iv) a nucleic acid sequence encoding a portion, numbered n, of the polypeptide of interest, and
(b) contacting said n polynucleotides with the type IIs restriction endonuclease and a ligase under conditions that allow for the cleavage of the n polynucleotides by said type IIs restriction endonuclease and the ligation of the resulting cleavage products, thereby producing the fusion polynucleotide encoding the polypeptide of interest.

Advantageously, it was shown in the studies underlying the present invention that the use of suitable type IIs cleavage sequences at the 3' or 5' ends of functional introns that are divided into two, non-functional moieties (a 5' end of a functional intron and a 3' end of a functional intron), allows for assembly of otherwise incompatible DNA fragments by type IIs restriction-ligation. Incompatible DNA fragments are equipped at their 5' and 3' termini with nucleic acid sequences representing such type IIs-split intron adapter modules. Golden Gate Cloning, i.e. the fusion of the fragments in desired order in a reaction comprising cleavage with a type IIs endonuclease and ligation, results in the reconstitution of functional introns by seamless ligation of split intron adapters that contain identical/compatible type IIs prefix and suffix sequences.

The method of the present invention, if applied, allows for a generic assembly of polynucleotides without the prerequisite of compatible sequences being part of sequence of the polynucleotides to be assembled. Accordingly, no alteration of the primary polynucleotide sequence is required. Thanks to the present invention, recombinatorial fusion of two or more polynucleotides, each encoding a portion of a polypeptide of interest is now possible as the cleavage sequences are provided by intron sequences (rather than by coding sequences). Concomitantly, otherwise incompatible DNA fragments will be assembled in a linear, yet intron-interspersed, fashion. Reconstituted intron "spacers" are removed upon transfection into a eukaryotic expression host after transcription by splicing to result in the intended, assembled nucleic acid construct. The method of the present invention, i.e. the combination of type IIs-based cloning with the split intron approach, thus provides a universal method to assemble coding DNA fragments independent of their sequence boundaries. The present invention, in particular, allows for an easy assembly of polynucleotides encoding different protein domains. If applied, it will allow for an easier production of proteins. Such proteins, can be, e.g. subjected to screening methods and may allow for the identification of proteins that have improved therapeutic properties. If applied, the method of the present invention will be a valuable tool in biologics drug discovery. The modular cloning described herein will allow a multispecific protein engineering. E.g., antibodies could be generated that are multispecific and thus have multiple targets. Such antibodies would have a broader spectrum of activity as compared to monospecific antibodies which have only a single target.

Unless stated otherwise, the definitions and explanations given herein above apply mutatis mutandis to the following.

Moreover, the present invention relates for producing a polypeptide of interest, comprising the steps of
(i) producing a fusion polynucleotide by the method of the present of invention, and
(ii) expressing said fusion polynucleotide in a eukaryotic host cell, thereby producing said polypeptide of interest.

In an embodiment, the method further comprises step (iii) of isolating the produced polypeptide of interest from said eukaryotic host cell. The term "isolating the produced polypeptide of interest from said eukaryotic host cells" also encompasses the isolation of the produced polypeptide from the supernatant of the culture medium.

In step (i), a fusion polynucleotide shall be produced by the method of the present of invention, i.e. by the method of producing a fusion polynucleotide encoding the polypeptide of interest. Thus, the steps of said method are carried out.

In step (ii), a fusion polynucleotide shall be expressed in a eukaryotic host cell, thereby producing said polypeptide of interest. How to express a polynucleotide is well known in the art and has been described above. In order to express said polynucleotide, it is preferably operably linked to a promoter. Said promoter shall be active in the host cell. Preferred host cells are described above.

The present invention also relates to a composition comprising a first polynucleotide as defined above and second polynucleotide. Said composition may further comprise a third polynucleotide as defined above. In addition to the first, second and third polynucleotide, said composition may comprise a fourth, or a fourth and fifth, or a fourth, fifth, and sixth, or a fourth, fifth, sixth, and seventh polynucleotide as defined above. Further, the composition may comprise one or more polynucleotides which do not comprise a portion of an intron, but suitable cleavage and recognition sites. Accordingly, said polynucleotide shall comprise a recognition site for the type IIs restriction endonuclease operably linked to a cleavage site that, upon cleavage with said type IIs restriction endonuclease, allows for ligating the polynucleotide to a further polynucleotide present in the composition. Said further polynucleotide shall have a cleavage site which is compatible to the cleavage site of said polynucleotide. The term "operably linked" is defined elsewhere herein. The definition applies accordingly.

Said polynucleotides shall be separate polynucleotides. However, upon assembly by cleavage and ligation a single polynucleotide (i.e. the fusion polynucleotide as referred to herein) will be generated.

In a preferred embodiment, the composition of the present invention comprises a first, second and third polynucleotide,
wherein said first polynucleotide comprises, in 5' to 3' direction:
(i) a nucleic acid sequence encoding a first portion of the polypeptide of interest,
(ii) a nucleic acid sequence encoding a 5' portion of a first intron,
(iii) a first cleavage sequence for a type IIs restriction endonuclease, and
(iv) a recognition sequence for said type IIs restriction endonuclease, wherein the first cleavage sequence in (iii) is operably linked to the recognition sequence in (iv),
wherein said second polynucleotide comprises, in 5' to 3' direction:
(i) a recognition sequence for the type IIs restriction endonuclease,
(ii) a second cleavage sequence for the type IIs restriction endonuclease, wherein said second cleavage sequence is complementary to first cleavage sequence, wherein the second cleavage sequence in (ii) is operably linked to the recognition sequence in (i),
(iii) a nucleic acid sequence encoding a 3' portion of the first intron, (iv) a nucleic acid sequence encoding a second portion of the polypeptide of interest,
(v) a nucleic acid sequence encoding a 5' portion of a second intron,
(vi) a third cleavage sequence for the type IIs restriction endonuclease, which differs from the first cleavage sequence of the first polynucleotide, and
(vii) a recognition sequence for the type IIs restriction endonuclease, wherein the third cleavage sequence in (vi) is operably linked to the recognition sequence in (vii), and
wherein said third polynucleotide comprises, in 5' to 3' direction:
(i) a recognition sequence for the type IIs restriction endonuclease
(ii) a fourth cleavage sequence for the type IIs restriction endonuclease, wherein said fourth cleavage sequence is complementary to the third cleavage sequence, wherein the fourth cleavage sequence in (ii) is operably linked to the recognition sequence in (i),
(iii) a nucleic acid sequence encoding a 3' portion of a second intron, and
(iv) a nucleic acid sequence encoding a third portion of the polypeptide of interest.

In addition to the polynucleotides as referred to above, the composition may further comprise a ligase, in particular a DNA ligase such as a T4 DNA ligase, and a type IIs restriction endonuclease. Said type IIs restriction endonuclease shall be capable of cleaving the polynucleotide at the, i.e. at all, cleavage sequences. Thus, said type IIs restriction endonuclease shall recognize the recognition sequence.

In a preferred embodiment of the composition of the present invention, the type IIs restriction endonuclease and the ligase comprised by the composition shall allow for the cleavage of the polynucleotides comprised by the composition (e.g. the first polynucleotide, second polynucleotide and third polynucleotide) and the ligation of the resulting cleavage products, thereby generating the fusion polynucleotide encoding the polypeptide of interest.

The present invention also relates to a kit comprising a first and second polynucleotide as defined above, a type IIs restriction endonuclease that allows for the cleavage of (i.e. which is capable of cleaving) the polynucleotides, and a ligase that allows for the ligation for cleavage products that result from the cleavage with said type IIs restriction endonuclease.

Said kit may further comprise a third polynucleotide as defined above. In addition to the first, second and third polynucleotide, said kit may comprise a fourth, or a fourth and fifth, or a fourth, fifth, and sixth, or a fourth, fifth, sixth, and seventh polynucleotide as defined above.

The present invention further concerns a polynucleotide encoding a polypeptide of interest, which, when transcribed in a eukaryotic host cell, is transcribed into a transcript comprising at least three introns which are heterologous to said polynucleotide.

The term "at least three introns" means three, or more than three, in particular at least four, at least five, at least six, at least seven, at least eight, at least nine, at least ten or at least 15 introns. Preferably, all introns comprised by the transcript are heterologous to said polynucleotide. The term "heterologous" has been described above.

The term "intron" has been defined above. The definition applies accordingly.

In an embodiment, all introns transcribed by the transcript are identical or essentially identical. In another embodiment, at least one intron differs from all other introns. In yet another embodiment, all introns differ from each other.

The length of the introns comprised by the transcript may be a length as specified herein above in connection with the method of the present invention. In an embodiment of the polynucleotide (or of the method) of the present invention, each of said introns comprised by the transcript has a length of 50 to 200 nt, in particular of 50 to 150 nt. E.g., each of said introns has a length of 50 to 100 nt. Further, each of said introns may have a length of 80 to 110 nt.

As described elsewhere herein, the intron(s) of the produced polynucleotide may also have (have) a length of at least 80 nucleotides, in particular at least 90 nucleotides. In a preferred embodiment, the intron(s) have a length of 80 to 200 nt. In another embodiment, the intron(s) has a length of 80 to 150 nt, such as a length of 80 to 120 nt. Further, it is envisaged that the intron(s) has (have) a length of 90 to 150 nt, such as a length of 90 to 120 nt.

Further, it is envisaged by the present invention that each intron comprised by the transcript comprises an internal stop codon in frame with the open reading frame of the nucleic acid sequence encoding the polypeptide of interest.

Finally, the present invention relates to the use of a composition comprising a ligase and a type IIs restriction endonuclease for producing a fusion polynucleotide encoding a polypeptide of interest by cleavage of
(a1) the first polynucleotide as defined above, and
(a2) the second polynucleotide as defined above, and optionally
(a3) the third polynucleotide as defined above, with said endonuclease, and ligation of the resulting cleavage products.

In accordance with the aforementioned use, at least one further polynucleotide may be cleaved, wherein said further polynucleotide is selected from the group consisting of:
(a4) the fourth polynucleotide as defined above,
(a5) the fifth polynucleotide as defined above,
(a6) the sixth polynucleotide as defined above, and
(a7) the seventh polynucleotide as defined above.

Preferred embodiments of the present invention are summarized herein below. The explanations and definition provided herein above apply mutatis mutandis to the following preferred embodiments:

1. A method for producing a fusion polynucleotide encoding a polypeptide of interest, said method comprising the steps of:
   (a1) providing a first polynucleotide, said first polynucleotide comprising, in 5' to 3' direction,
      (i) a nucleic acid sequence encoding a first portion of the polypeptide of interest,
      (ii) a nucleic acid sequence encoding a 5' portion of a first intron,
      (iii) a first cleavage sequence for a type IIs restriction endonuclease, and
      (iv) a recognition sequence for the type IIs restriction endonuclease, wherein the first cleavage sequence in (iii) is operably linked to the recognition sequence in (iv),
   (a2) providing a second polynucleotide, said second polynucleotide comprising, in 5' to 3' direction,
      (i) a recognition sequence for the type IIs restriction endonuclease,
      (ii) a second cleavage sequence for the type IIs restriction endonuclease, wherein said second cleavage sequence is complementary to first cleavage sequence, and wherein the second cleavage sequence in (ii) is operably linked to the recognition sequence in (i),
(iii) a nucleic acid sequence encoding a 3' portion of the first intron, and
(iv) a nucleic acid sequence encoding a second portion of the polypeptide of interest, and
(b) contacting said first polynucleotide and second polynucleotide with the type IIs restriction endonuclease and a ligase under conditions that allow for the cleavage of the first polynucleotide and second polynucleotide by said type IIs restriction endonuclease and the ligation of the resulting cleavage products, thereby producing the fusion polynucleotide encoding the polypeptide of interest.

2. The method of embodiment 1, wherein said fusion polynucleotide comprises, in 5' to 3' direction:
(aa) the nucleic acid sequence encoding the first portion of the polypeptide of interest,
(bb) a nucleic acid sequence encoding a first intron, wherein said first intron is functional, and wherein said first intron comprises the nucleic acid sequence encoding the 5' portion of the first intron and the nucleic acid sequence encoding the 3' portion of the first intron, and
(cc) the nucleic acid sequence encoding the second portion of the polypeptide of interest.

3. The method of embodiments 1 and 2, wherein said fusion polynucleotide, when transcribed in a eukaryotic host cell, is transcribed into a transcript that is processed in said cell so that the intron is spliced out of said transcript, thereby producing a mRNA encoding the polypeptide of interest.

4. The method of any one of embodiments 1 to 3, wherein the first intron is heterologous to the fusion polynucleotide.

5. The method of any one of embodiments 1 to 4, wherein the polynucleotide encoding the first intron has a length of 40 to 2000 bp.

6. The method of any one of embodiments 1 to 5, wherein the polynucleotide encoding the intron has a length of 50 to 200 bp, in particular of 50 to 150 bp.

7. The method of any one of embodiments to 1 to 6, wherein said first intron comprises an internal stop codon in frame with the open reading frame of the nucleic acid sequence encoding the polypeptide of interest.

8. The method of any one of embodiments 1 to 7, wherein said second polynucleotide further comprises
(v) a nucleic acid sequence encoding a 5' portion of a second intron,
(vi) a third cleavage sequence for the type IIs restriction endonuclease, which differs from the third cleavage sequence of the first polynucleotide, and
(viii) a recognition sequence for the type IIs restriction endonuclease, wherein the third cleavage sequence in (vi) is operably linked to the recognition sequence in (vii).

9. The method of embodiment 8, wherein said method further comprises
(a3) providing a third polynucleotide, said third polynucleotide comprising, in 5' to 3' direction,
(i) a recognition sequence for the type IIs restriction endonuclease,
(ii) a fourth cleavage sequence for the type IIs restriction endonuclease, wherein said fourth cleavage sequence is complementary to the third cleavage sequence, wherein the fourth cleavage sequence in (ii) is operably linked to the recognition sequence in (i),
(iii) a nucleic acid sequence encoding a 3' portion of a second intron, and
(iv) a nucleic acid sequence encoding a third portion of the polypeptide of interest,
wherein in step (b) said first polynucleotide, second polynucleotide and third polynucleotide are contacted with the type IIs restriction endonuclease and a ligase under conditions that allow for the cleavage of the first polynucleotide, second polynucleotide and third polynucleotide by said type IIs restriction endonuclease and the ligation of the resulting cleavage products, thereby producing the fusion polynucleotide encoding the polypeptide of interest, and
wherein said fusion polynucleotide comprises, in 5' to 3' direction,
(aa) the nucleic acid sequence encoding the first portion of the polypeptide of interest,
(bb) a nucleic acid sequence encoding a first intron, wherein said first intron is functional, and wherein said first intron comprises the nucleic acid sequence encoding the 5' portion of the first intron and the nucleic acid sequence encoding the 3' portion of the first intron,
(cc) the nucleic acid sequence encoding the second portion of the polypeptide of interest,
(dd) a nucleic acid sequence encoding a second intron, wherein said second intron is functional, and wherein said second intron comprises the nucleic acid sequence encoding the 5' portion of the second intron and the nucleic acid sequence encoding the 3' portion of the second intron, and
(ee) the nucleic acid sequence encoding the third portion of the polypeptide of interest.

10. A method for producing a polypeptide of interest, comprising the steps of
(i) producing a fusion polynucleotide encoding the polypeptide of interest by the method according to any one of embodiments 1 to 9, and
(ii) expressing said fusion polynucleotide in a eukaryotic host cell, thereby producing said polypeptide of interest.

11. The method of embodiment 10, wherein the method further comprises step (iii) of isolating the produced polypeptide of interest from said eukaryotic host cell.

12. A composition, comprising a first, second and third polynucleotide,
wherein said first polynucleotide comprises, in 5' to 3' direction:
(i) a nucleic acid sequence encoding a first portion of the polypeptide of interest,
(ii) a nucleic acid sequence encoding a 5' portion of a first intron,
(iii) a first cleavage sequence for a type IIs restriction endonuclease, and
(iv) a recognition sequence for said type IIs restriction endonuclease, wherein the first cleavage sequence in (iii) is operably linked to the recognition sequence in (iv),
wherein said second polynucleotide comprises, in 5' to 3' direction:
(i) a recognition sequence for the type IIs restriction endonuclease,
(ii) a second cleavage sequence for the type IIs restriction endonuclease, wherein said second cleavage sequence is complementary to first cleavage sequence, wherein the second cleavage sequence in (ii) is operably linked to the recognition sequence in (i), (iii) a nucleic acid sequence encoding a 3' portion of the first intron,
(iv) a nucleic acid sequence encoding a second portion of the polypeptide of interest,
(v) a nucleic acid sequence encoding a 5' portion of a second intron,
(vi) a third cleavage sequence for the type IIs restriction endonuclease, which differs from the first cleavage sequence of the first polynucleotide, and
(vii) a recognition sequence for the type IIs restriction endonuclease, wherein the third cleavage sequence in (vi) is operably linked to the recognition sequence in (vii), and wherein said third polynucleotide comprises, in 5' to 3' direction:
(i) a recognition sequence for the type IIs restriction endonuclease
(ii) a fourth cleavage sequence for the type IIs restriction endonuclease, wherein said cleavage sequence is complementary to the third cleavage sequence, wherein the fourth cleavage sequence in (ii) is operably linked to the recognition sequence in (i),
(iii) a nucleic acid sequence encoding a 3' portion of a second intron, and
(iv) a nucleic acid sequence encoding a third portion of the polypeptide of interest.

13. The composition of embodiment 12, wherein said composition further comprises the type IIs restriction endonuclease and a ligase.

14. The composition of embodiment 13, wherein said type IIs restriction endonuclease and said ligase allow for the cleavage of the first polynucleotide, second polynucleotide and third polynucleotide and the ligation of the resulting cleavage products, thereby generating the fusion polynucleotide encoding the polypeptide of interest.

15. A kit comprising a first, second and third polynucleotide as defined in embodiment 12, a type IIs restriction endonuclease that allows for the cleavage of the first polynucleotide, second polynucleotide and third polynucleotide, and a ligase that allows for the ligation for cleavage products that result from the cleavage with said type IIs restriction endonuclease.

16. The method of any one of embodiments 1 to 10, the composition of any one of embodiments 11 to 14, or the kit of embodiment 15, wherein said type IIs restriction endonuclease is selected from AcuI, AlwI, BaeI, BbsI, BbvI, BccI, BceAI, BcgI, BciVI, BcoDI, BfuAI, BmrI, BpmI, BpuEI, BsaI, BsaXI, BseRT, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, and SfaNI.

17. A polynucleotide encoding a polypeptide of interest, which, when transcribed in a eukaryotic host cell, is transcribed into a transcript comprising at least five introns which are heterologous to said polynucleotide.

18. The polynucleotide of embodiment 17, wherein said polynucleotide is transcribed into a transcript comprising at least seven introns which are heterologous to said polynucleotide.

19. The polynucleotide of embodiment 17 and 18, wherein each of said introns has a length of 50 to 200 nt, in particular of 50 to 150 nt.

20. The polynucleotide of any one of embodiments 17 to 19, wherein each of said introns has a length of 80 to 200 nt, such as a length of 90 to 150 nt or 90 to 120 nt.

21. The polynucleotide of embodiment 19, wherein each of said introns has a length of 50 to 100 nt.

22. The polynucleotide of any one of embodiments 17 to 21, wherein all introns comprise an internal stop codon in frame with the open reading frame of the nucleic acid sequence encoding the polypeptide of interest.

23. Use of a composition comprising a ligase and a type IIs restriction endonuclease for producing a fusion polynucleotide encoding a polypeptide of interest by cleavage of
(a1) the first polynucleotide as defined in embodiment 1, and
(a2) the second polynucleotide as defined in embodiment 1 or 3, and optionally
(a3) the third polynucleotide as defined in embodiment 3, with said endonuclease, and ligation of the resulting cleavage products.

All references cited in this specification are herewith incorporated by reference with respect to their entire disclosure content and the disclosure content specifically mentioned in this specification.

EXAMPLES

The invention will be merely illustrated by the following Examples. The said Examples shall, whatsoever, not be construed in a manner limiting the scope of the invention.

Example 1: Material & Methods

Plasmids
(a) Cloning of Constructs Containing Luciferase(s)
Plasmid pcDNA5-FRT-TO_DEST (based on pcDNA5/FRT/TO from Invitrogen/ThermoFisher Scientific and modified to allow for Gateway cloning by inserting attR1/2 sites between the CMV promoter and the BGHpA site) was adjusted to allow for concomitant expression of Renilla and Firefly luciferases (hRluc and luc2, respectively—see FIG. 1) as follows: (i) the promoter of the eukaryotic elongation factor 1α (EF1a) was introduced by blunt ligation into the PmlI site of pcDNA5-FRT-TO_DEST, destroying the 5' PmeI but keeping the 3' site thereby creating pcDNA5dual-FRT-TO DEST. (ii) The Firefly luciferase nucleotide sequence (amino acid sequence taken from pGL4.10 [Promega], gene synthesis with codon optimization for expression in human cell lines was done by GeneArt/Thermo Fisher Scientific, Regensburg). A 5' consensus Kozak sequence (CACGTGAGCGCCACC, SEQ ID NO 43) at its 5' end and a double stop codon (TAATGA) at its 3' end was inserted into the PmlI site of pcDNA5dual-FRT-TO_DEST resulting in luc2-pcDNA5dual-FRT-TO DEST. (iii) All Renilla luciferase nucleotide sequences (the amino acid sequence of Renilla luciferase was taken from pGL4.75 [Promega]) with intron sequences were synthesized by GeneArt/Thermo Fisher Scientific, Regensburg (codon optimized as above) with flanking attB1 and attB2 sequences including a 5' Kozak consensus sequence and a 3' double stop codon (ACTTTGTACAAAAAAGCAGG CTAGCGCCACC (SEQ ID NO: 44) and TGATAAGCT-TACCCAGCTTTCTTGTACAAAG (SEQ ID NO: 45), respectively) to allow for Gateway cloning into luc2-pcDNA5dual-FRT-TO_DEST (for the exact intron positions see FIGS. 2 & 8). (iv) Similarly, an intron-less Renilla luciferase was cloned into the pcDNA5dual-FRT-TO_DEST (without the Firefly luciferase gene) which was used as main positive control in all Renilla luciferase assays.

(b) Cloning of Antibody Constructs (Standard Restriction and Golden Gate-Based Cloning)

Conventional CMV-based vectors for transient expression in eukaryotic cells were used to generate antibody expression constructs (light and heavy chain constructs) using either restriction cloning (inserts contained a Kozak consensus sequence) or Golden Gate cloning. For the latter, BsaI restriction sites were removed from the vector backbone and a stuffer sequence was introduced flanked by BsaI sites (5': cgccagGAGACC (SEQ ID NO: 46), 3: GGTCTC-tataat (SEQ ID NO: 47); BsaI recognition sequence in bold) used for the integration of the antibody sequences into the expression vector. The antibody constructs (all anti-huIL4) were assembled using varying combinations of modules containing different introns and were then cloned into the expression vector as described by Weber et al (PLoS ONE. 2011 Feb. 18; 6(2):e16765) and Engler et al (ACS Synth Biol. 2014 Nov. 21; 3(11):839-43). The nucleotide sequence of the coding sequence of the antibody constructs were identical in both intron-less and intron-containing antibodies with the exception of (i) one nucleotide in the constant region of the heavy chain where (for those constructs created using Golden Gate-based cloning) a BsaI site needed to be destroyed, and (ii) the last codon of the leader sequences.

Golden Gate Modules

Golden Gate modules to create antibody light and heavy chains containing introns were designed to contain three parts: the 3' part of an intron was placed at the 5' end of a module, followed by the coding sequence of a domain, i.e. either the variable or constant part of the antibody chain. The coding sequence was then followed by the 5' part of the next intron. At both ends BsaI sites were placed in such a way that these sites are removed upon digestion with BsaI leaving a 4 nucleotide overhang specific for each intron position thus allowing for specific ligation and assembly of the final construct.

Introns

A set of introns was used in the studies underlying the present invention: original, modified and partial introns:

An overview on the introns can be found in Tables 1 to 4. Modified or partial introns comprised:

(a) introns with a deletion of canonical splice sites at either 5' or 3' ends of the introns to be used as negative controls (introns #10-#13)

(b) introns with 4 nucleotide insertions (as an example for inserted overlap sequences for the Golden Gate cloning reaction; introns #14-#16 & #19-#20)

(c) introns with larger nucleotide inserts containing two potential overlap sequences at either side of the insert (which could be used for skipping of exons; introns #17-#18)

(d) hybrid introns consisting of two halves of different introns (introns #21-24)

(e) partial introns that consisted of either a 5' part or a 3' part of its original introns for use in Golden Gate cloning reaction (partial introns #1-#16)

TABLE 1

Original introns (for the sequence and further comments, please see Table 3)

| Intron # | Intron ID | Intron Name | Reference | Intron Type | Intron Number/ Total Number Of Introns | Intron Length [bp] | Natural 5' Flanking Sequence | Natural 3' Flanking Sequence | Frame-shift | Contains In-Frame Stop Codon |
|---|---|---|---|---|---|---|---|---|---|---|
| 1 | I1 | HNRNPH1-I7 | Shimada et al. (2015). Int. J. Mol. Sci. (2015) 16, 10376: SN10 | native | 7/13 | 56 | GAG | ACC | yes | yes |
| 2 | I2 | SIGLEC6-I1 | Shimada et al. (2015). Int. J. Mol. Sci. (2015) 16, 10376: SN12 | native | 1/7 | 62 | CAG | GGG | yes | yes |
| 3 | I3 | PLXNA1-I10 | Shimada et al. (2015). Int. J. Mol. Sci. (2015) 16, 10376: SN17 | native | 10/28 | 65 | AGG | CGC | yes | no |
| 4 | I4 | ADAM11-I7 | Shimada et al. (2015). Int. J. Mol. Sci. (2015) 16, 10376: SN22 | native | 7/26 | 65 | CAG | GCT | yes | no |
| 5 | I5 | MUSIGHID1-I1 | Jäger et al. (2013). BMC Biotechnology (2013) 13, 52; Genbank: M12880.1; Invitrogen: pCMV/ER/myc | native | pre-sumably 1/1 | 82 | CAG | GCG | yes | yes |
| 6 | I6 | PG-SZ-1 | — | native | ? | 375 | CAG | GGC | no | yes |
| 7 | I7 | Xiao_JBi-1 | Xiao et al. (2015). PLos One 10, e140691: pSplicev5.1-1 | poten-tially hybrid | n.a. | 72 | NNG | n.a. | no | yes |
| 8 | I8 | MUSIGCD10-I1 | Lacy-Hulbert et al. (2001). Gene Therapy 8, 649; Genbank: AH005309.2 | native | — | 110 | CCC | GGG | yes | yes |

TABLE 1-continued

Original introns (for the sequence and further comments, please see Table 3)

| Intron # | Intron ID | Intron Name | Reference | Intron Type | Intron Number/ Total Number Of Introns | Intron Length [bp] | Natural 5' Flanking Sequence | Natural 3' Flanking Sequence | Frame-shift | Contains In-Frame Stop Codon |
|---|---|---|---|---|---|---|---|---|---|---|
| 9 | I9 | MUSIGCE01-I3 | Lacy-Hulbert et al. (2001). Gene Therapy 8, 649; Genbank: AH001924.2 | native | — | 82 | CAG | CTG | yes | yes |

TABLE 2

Modified ("artificial") introns (for the sequence and further comments, please see Table 3)

| Intron # | Intron ID | Intron Name | Intron Type | Intron Length [bp] | Natural 5' Flanking Sequence | Natural 3' Flanking Sequence | Frame-shift | Contains In-Frame Stop Codon |
|---|---|---|---|---|---|---|---|---|
| 10 | I2(del5ss) | SIGLEC6-I1(del5ss) | destroyed | 62 | CAG | GGG | yes | yes |
| 11 | I2(del3ss) | SIGLEC6-I1(del3ss) | destroyed | 62 | CAG | GGG | yes | yes |
| 12 | I3(del5ss) | PLXNA1-I10(del5ss) | destroyed | 65 | AGG | CGC | yes | no |
| 13 | I3(del3ss) | PLXNA1-I10(del3ss) | destroyed | 65 | AGG | CGC | yes | no |
| 14 | I3(ins38)-1 | PLXNA1-I10(ins38CAAG) | modified | 69 | AGG | CGC | no | yes |
| 15 | I3(ins38)-2 | PLXNA1-I10(ins38CAGC) | modified | 69 | AGG | CGC | no | yes |
| 16 | I3(ins38)-3 | PLXNA1-I10(ins38TTCC) | modified | 69 | AGG | CGC | no | yes |
| 17 | I3(ins38)-4 | PLXNA1-I10(ins38CAAGtgggctGAGG) | modified | 79 | AGG | CGC | yes | no |
| 18 | I3(ins38)-5 | PLXNA1-I10(ins38CAGCtgggctGCTT) | modified | 79 | AGG | CGC | yes | no |
| 19 | I3(ins37)-1 | PLXNA1-I10(ins37CAAG) | modified | 69 | AGG | CGC | yes | yes |
| 20 | I3(ins37)-2 | PLXNA1-I10(ins37CAGC) | modified | 69 | AGG | CGC | yes | yes |
| 21 | I3(1-29)_I8(25-110) | PLXNA1-I10(1-29)_MUSIGCD10-I1(25-110) | hybrid | 115 | AGG | GGG | yes | yes |
| 22 | I3(1-48)_I8(99-110) | PLXNA1-I10(1-48)_MUSIGCD10-I1(99-110) | hybrid | 60 | AGG | GGG | no | no |
| 23 | I8(1-24)_I3(30-65) | MUSIGCD10-I1(1-24)_PLXNA1-I10(30-65) | hybrid | 60 | CCC | CGC | no | yes |
| 24 | I8(1-98)_I3(49-65) | MUSIGCD10-I1(1-98)_PLXNA1-I10(49-65) | hybrid | 115 | CCC | CGC | yes | yes |

TABLE 3

Sequences of the introns in Table 1 and 2-Comments

| Intron # | Intron ID | Intron Sequence (putative Branch Site) | SEQ ID NO | Comment |
|---|---|---|---|---|
| 1 | I1 | GTAAGGTAAGAATTGAATTTCTCAGTTGAAGGATGCTT ACACTCTTGTCCATCTAG | 1 | no expression; probably needs enhancer element in flanking exons according to Sasaki-Haraguchi et al (2012) in order to be a functional intron |
| 2 | I2 | GTGAGTGGGCCAGGGGAGAGGTGCCGTGGGCTGGGCCGAGCTGACCCTCAT**GTCTCCATAG | 2 | unclear whether this intron contains an intronic splicing suppressor (ISS) or an enhancer (ISE); according to the text Shimada et al (2015)/Sasaki-Haraguchi et al. |

TABLE 3-continued

Sequences of the introns in Table 1 and 2-Comments

| Intron # | Intron ID | Intron Sequence (putative Branch Site) | SEQ ID NO | Comment |
|---|---|---|---|---|
| | | | | (2012) mention ISEs but a table in Shimada et al. states an ISS! double underlined sequence = ISE (or ISS) |
| 3 | I3 | GTGAGTGGGCGCCCCGGCGGGGTGGGCAGTGGGCGG GCCCGAGCTGACCGCACCCCTCCCCACAG | 3 | |
| 4 | I4 | GTAAGGGAGGGAAGGGGGGGTGGGGAGGGGCCGGC TGTGCCCCCCTCACCTGCCCCTCCCCACAG | 4 | |
| 5 | I5 | GTAAGGGG<u>TT</u><u>A</u>ACAGTAGCAGGCTTGAGGTCTGGACA TATATATGGGTGACAATGACATCCACTTTGCCTTTCTCT CCACAG | 5 | pCSE2.5-vector derived from pCMV/ER/myc (Invitrogen); Genbank: MI2880.1 with 2 point mutations (double underlined) |
| 6 | I6 | GTAAGTCAGGTGTCAGCCGCAGATGCGTTCAGGTGAG GGCGGAGGCTAGCGGGGCGCTGTGCAGCACTGAGCTC GCGGAAGACCAGGACCAGGAGATCACCGAGGGCGACC GCCAGGCCCCGGGCCCTCCGCTCCCGAGGGGCGGCCT CTCAGCACCAGCCCGGGGGCCGGCCTGATCGCCACGC AGGCACCTGCCGCCGCCACCGCCACCGCCATCTCAACC GTACGGGTGGGAGAGGCTGTGCGCCGCTCCAGGGGA GATCCGGCTCCCATCCGGCCCCACCCGCCCTGCCTTGCC CTGCCCGCAGCTTCTGGGCTGCCAGGCTCCATTCTGAA GCTTCTACTAACTCTCGAGTCTTCTTTTTTTTTTCACAG | 6 | sequence of a longer intron |
| 7 | I7 | GTAAGTCAACGCAATTAATCTATGAAATCCCTAATGCCT ACGGCAGCCGCTGGATTGTTACTTCTTCTTCAG | 7 | |
| 8 | I8 | GTAAGAACCAAACCCTCCCAGCAGGGGTGCCCAGGCCC AGGCATGCCCAGAGGGAGCAGCGGGTGGGGCTTAG GCCAAGCTGAGCTCACACCTTGACCTTTCATTCCAG | 8 | first intron of the mouse Cμ gene; naming as in paper |
| 9 | I9 | GTGAGTACAGGAGGTGGAGAGTGGCCAGCCCTTCTCA TGTTCAGAGAACATGGTTAACTGGTTAAGTCATGTCGT CCCACAG | 9 | third intron of the mouse Cε gene; naming as in paper |
| 10 | I2(del5ss) | tgGAGTGGGCCAGGGGAGAGGTGCCGTGGGGCTGGGC CGAGCTGACCCTCATGTCTCCATAG | 10 | GT → tg, 5' splice site destroyed |
| 11 | I2(del3ss) | GTGAGTGGGCCAGGGGAGAGGTGCCGTGGGGCTGGG CCGAGCTGACCCTCATGTCTCCATga | 11 | AG → ga, 3' splice site destroyed |
| 12 | I3(del5ss) | tgGAGTGGGCGCCCCGGCGGGGTGGGCAGTGGGCGG GCCCGAGCTGACCGCACCCCTCCCCACAG | 12 | GT → tg, 5' splice site destroyed |
| 13 | I3(del3ss) | GTGAGTGGGCGCCCCGGCGGGGTGGGCAGTGGGCGG GCCCGAGCTGACCGCACCCCTCCCCACga | 13 | AG → ga, 3' splice site destroyed |
| 14 | I3(in538)-1 | GTGAGTGGGCGCCCCGGCGGGGTGGGCAGTGGGCGG GCAAGCCCGAGCTGACCGCACCCCTCCCCACAG | 14 | |
| 15 | I3(in538)-2 | GTGAGTGGGCGCCCCGGCGGGGTGGGCAGTGGGCGG GCAGCCCCGAGCTGACCGCACCCCTCCCCACAG | 15 | |
| 16 | I3(in538)-3 | GTGAGTGGGCGCCCCGGCGGGGTGGGCAGTGGGCGG GTTCCCCCGAGCTGACCGCACCCCTCCCCACAG | 16 | |
| 17 | I3(in538)-4 | GTGAGTGGGCGCCCCGGCGGGGTGGGCAGTGGGCGG GCAAGTGGGCTGAGGCCCGAGCTGACCGCACCCCTCC CCACAG | 17 | |
| 18 | I3(ins38)-5 | GTGAGTGGGCGCCCCGGCGGGGTGGGCAGTGGGCGG GCAGCTGGGCTGCTTCCCGAGCTGACCGCACCCCTCC CACAG | 18 | |
| 19 | I3(in537)-1 | GTGAGTGGGCGCCCCGGCGGGGTGGGCAGTGGGCGG CAAGGCCCGAGCTGACCGCACCCCTCCCCACAG | 19 | |
| 20 | I3(ins37)-2 | GTGAGTGGGCGCCCCGGCGGGGTGGGCAGTGGGCGG CAGCGCCCGAGCTGACCGCACCCCTCCCCACAG | 20 | |

TABLE 3-continued

Sequences of the introns in Table 1 and 2-Comments

| Intron # | Intron ID | Intron Sequence (putative Branch Site) | SEQ ID NO | Comment |
|---|---|---|---|---|
| 21 | I3(1-29)_I8(25-110) | GTGAGTGGGCGCCCCGGCGGGGTGGGCAGGGGTGCCCAGGCCCAGGCATGGCCCAGAGGGAGCAGCGGGTGGGGCTTAGGCCAAGCTGAG<u>CTCAC</u>ACCTTGACCTTTCATTCCAG | 21 | I3 part (5' end) in bold and underlined |
| 22 | I3(1-48)_I8(99-110) | GTGAGTGGGCGCCCCGGCGGGGTGGGCAGTGGGCGGGCCCGAGCTGACCTTTCATTCCAG | 22 | I3 part (5' end) in bold and underlined |
| 23 | I8(1-24)_I3(30-65) | GTAAGAACCAAACCCTCCCAGCAGTGGGCGGGCCCGAGCTGACCGCACCCCTCCCCACAG | 23 | I3 part (3' end) in bold and underlined |
| 24 | I8(1-98)_I3(49-65) | GTAAGAACCAAACCCTCCCAGCAGGGGTGCCCAGGCCCAGGCATGGCCCAGAGGGAGCAGCGGGTGGGGCTTAGGCCAAGCTGAG<u>CTCAC</u>ACCTTGACCGCACCCCTCCCCACAG | 24 | I3 part (3' end) in bold and underlined |

TABLE 4

Partial introns-Positions in the 5' part ("N") of the partial introns include the overlap sequence used for cloning with the exception of artificially inserted sequences; the 3' part ("C") of the partial introns start directly after the overlap sequence.

| Partial Intron # | Intron ID | Intron Name | Alias | Intron Type | Partial Intron Length [bp] | Natural 5' Flanking Sequence | Intron Sequence (putative Branch Site, Cloning Overlap Sequence) | Natural 3' Flanking Sequence | Comment |
|---|---|---|---|---|---|---|---|---|---|
| 1 | I3N1(1-29) | PLXNA1-I10(1-29) | I3N1 | partial | 29 | AGG | GTGAGTGGGCGCCCCGGCGGGGTGGGCA G (SEQ ID NO: 25) | | |
| 2 | I3C1(30-65) | PLXNA1-I10(30-65) | I3C1 | partial | 36 | | TGGGCGGGCCCGAGCTGACCGCACCCCTCC CCACAG (SEQ ID NO: 26) | CGC | |
| 3 | I3N2(1-48) | PLXNA1-I10(1-48) | I3N2 | partial | 48 | AGG | GTGAGTGGGCGCCCCGGCGGGGTGGGCA GTGGGCGGGCCCGAGCTGAC (SEQ ID NO: 27) | | |
| 4 | I3C2(49-65) | PLXNA1-I10(49-65) | I3C2 | partial | 17 | | CGCACCCCTCCCCACAG (SEQ ID NO: 28) | CGC | |
| 5 | mI3N1 (1-36_insCAAG) | PLXNA1-I10(1-36_insCAAG) | mI3N1 | partial | 40 | AGG | GTGAGTGGGCGCCCCGGCGGGGTGGGCA GTGGGCGGCAAG (SEQ ID NO: 29) | | cloning overlap sequence = insert sequence |
| 6 | mI3C1 (insCAAG_37-65) | PLXNA1-I10 (insCAAG_37-65) | mI3C1 | partial | 29 | | GCCCGAGCTGACCGCACCCCTCCCCACAG (SEQ ID NO: 30) | CGC | |
| 7 | mI3N2 (1-36_insCAGC) | PLXNA1-I10(1-36_insCAGC) | mI3N2 | partial | 40 | AGG | GTGAGTGGGCGCCCCGGCGGGGTGGGCA GTGGGCGGCAGC (SEQ ID NO: 31) | | cloning overlap sequence = insert sequence |
| 8 | mI3C2 (insCAGC_37-65) | PLXNA1-I10 (insCAGC_37-65) | mI3C2 | partial | 29 | | GCCCGAGCTGACCGCACCCCTCCCCACAG (SEQ ID NO: 32) | CGC | |
| 9 | I8N1 (1-24) | MUSIGCD10-I1(1-24) | I8N1 | partial | 24 | CCC | GTAAGAACCAAACCCTCCCAGCAG (SEQ ID NO: 33) | | |
| 10 | I8C1 (25-110) | MUSIGCD10-I1(25-110) | I8C1 | partial | 86 | | GGGTGCCCAGGCCCAGGCATGGCCCAGAG GGAGCAGCGGGTGGGCTTAGGCCAAGCT GAGCTCACACCTTGACCTTTCATTCCAG (SEQ ID NO: 34) | GGG | |

TABLE 4-continued

Partial introns-Positions in the 5' part ("N") of the partial introns include the overlap sequence used for cloning with the exception of artificially inserted sequences; the 3' part ("C") of the partial introns start directly after the overlap sequence.

| Partial Intron # | Intron ID | Intron Name | Alias | Intron Type | Partial Intron Length [bp] | Natural 5' Flanking Sequence | Intron Sequence (putative Branch Site, Cloning Overlap Sequence) | Natural 3' Flanking Sequence | Comment |
|---|---|---|---|---|---|---|---|---|---|
| 11 | I8N2 (1-98) | MUSIGCD10-I1(1-98) | I8N2 | partial | 98 | CCC | GTAAGAACCAAACCTCCCAGCAGGGGTGC CCAGCCCAGGCATGGCCCAGAGGAGCA GCGGGTGGGCTTAGGCCAAGCTGAGCTC ACACCTTGAC (SEQ ID NO: 35) | | |
| 12 | I8C2 (99-110) | MUSIGCD10-I1(99-110) | I8C2 | partial | 12 | | CTTTCATTCCAG (SEQ ID NO: 36) | GGG | |
| 13 | I9N1 (1-22) | MUSIGCE01-I3(1-22) | I9N1 | partial | 22 | CAG | GTGAGTACAGGAGGTGGAGAGT (SEQ ID NO: 37) | | |
| 14 | I9C1 (23-82) | MUSIGCE01-I3(23-82) | I9C1 | partial | 60 | | GGCCAGCGCCTTCTCATGTTCAGAGAACATG GTTAACTGGTTAAGTCATGTCGTCCCACAG (SEQ ID NO: 38) | CTG | |
| 15 | I9N2 (1-60) | MUSIGCE01-I3(1-60) | I9N2 | partial | 60 | CAG | GTGAGTACAGGAGGTGGAGAGTGCCAGC CCTTCTCATGTTCAGAGAACATGGTTAACTG (SEQ ID NO: 39) | | |
| 16 | I9C2 (61-82) | MUSIGCE01-I3(61-82) | I9C2 | partial | 22 | | GTTAAGTCATGTCGTCCCACAG (SEQ ID NO: 40) | CTG | |

Cell Culture and Transfection

Suspension-adapted HEK293-F cells (Invitrogen Cat. No. 51-002) were cultivated in Freestyle F17 Expression medium (Gibco Cat. No. A1383502) containing 6 mM glutamine. The day prior to transfection, 1 litre of cells were seeded at a density of 1.2e6 cells/ml in a 3 L Fernbach Erlenmeyer flask with vent cap (Corning 431252) and incubated over night at 37° C. with agitation at 110 rpm and 8% $CO_2$.

The day of transfection, the cells were adjusted to 1.9e6 cells/ml with F17 expression medium. For each transfection 50 ng pXL4617_EBNA (EBNA1 expression plasmid) were mixed with 1 µg DNA of the expression construct of interest and 2.8 µg PEI (Polysciences, Cat. No. 23966-2) and adjusted to a volume of 230 µl with F17 expression medium. After 15 min incubation 870 µl cells (1.65e6) were added to the DNA/PEI complex. All transfection experiments were conducted on 96-deep well plates (Nunc Cat. No. 10447181) in a final working volume of 1100 µl. The plates were covered with a DUETZ system lid (Kuehner Technology) and incubated for two days at 37° C., 8% $CO_2$ and 1,000 rpm shaking with 3 mm orbit (Infors HT Multitron Pro). All transfections were performed at least in duplicate and repeated 2-5 times.

Expression Analysis Using a Luciferase Reporter Assay (Luciferase Constructs)

(a) Experimental Procedure

The luciferase activity of the transfected cells was measured two days after transfection with the Dual-Glo® Luciferase Assay System (Promega, Cat. No. E2940). 50 µl cell suspension was transferred to a 96-well isoplate (Perkin Elmer Cat. No. 6005040)) and equilibrated for 10 min at room temperature. 50 µl Dual-Glo® reagent was added and incubated for 10 min to lyse the cells. The firefly luciferase luminescence was measured with a microplate reader (Molecular Devices, Gemini XP; Settings: 30 reads, high PMT). 50 µl Dual-Glo® Stop & Glo® reagent was added to quench the luminescence from the firefly reaction. After 10 min incubation the Renilla luciferase luminescence was measured under the same conditions as described for the firefly luciferase.

(b) Data Analysis

Multiple data points from one transfection (duplicates or triplicates) were used to create mean values. These were then normalized with respect to the mean signal of the bicistronic construct containing Renilla luciferase [hRLuc, without intron] together with Firefly luciferase [luc2]) resulting in a relative expression level. The mean value of the relative expression levels of two to nine experiments per tested construct was then calculated (together with the standard deviation).

Signals from measurements of the Firefly luciferase were used as a control to indicate successful transfection (data not shown).

Expression Analysis Using Octet® $QK^e$ (Antibody Constructs)

(a) Quantification

Seven days after transfection, the cell supernatants containing the expressed antibody constructs were harvested by centrifugation (3220 rcf, 2 min). These supernatants were quantified by bio-layer interferometry (BLI) using the Octet® $QK^e$ system (Pall FortéBio, #30-5046) using Protein A biosensors (Pall FortéBio, #18-5013). Quantification with regeneration of the biosensor was performed as follows: the cell supernatants were diluted 1:10 in D-PBS (Gibco, #14190-094) and transferred to the assay plate (Greiner microplates 96 well, PP, black, #655209). Quantification time was set to 120 sec, regeneration/neutralization of biosensors was done with 10 mM Glycine/HCl, pH 1.5 and D-PBS to 5 sec, using three cycles before the first measurement and between all following measurements. The assay was performed at 30° C. and shaking at 1000 rpm. The sensor offset was set to 3 mm. The experiment started after a delay of 600 sec to equilibrate the plate for 10 min (30° C. and shaking).

(b) Data Analysis

Data analysis was done using FortéBio Data Analysis 9.0 together with a pre-validated human IgG standard curve (binding rate versus concentration). Multiple data points from several transfections (each done in duplicate) were used to create mean values and standard deviations from three independent experiments.

Binding Assays Using Octet® $QK^e$ (a) Antibody Binding on Human IL4

The Octet® $QK^e$ system was also used to test the dissociation rate ($k_d$) of the expressed anti-IL4 antibodies from human IL4. To this end 2.5 µg/mL recombinant human IL4 (novoprotein, #CD88) with a His6 tag was captured on biosensors (HIS1K, Pall FortéBio, #18-5122) pre-coated with anti-penta-His antibody (Qiagen) for 120 sec. After baseline recording using supernatant from mock transfections ("baseline wells", diluted 1:10 in D-PBS, loading time 30 sec) the biosensors were dipped into the sample wells containing the sample supernatants (also diluted 1:10 in D-PBS). After 120 sec of incubation, the biosensors were moved back to the supernatants of the baseline wells to allow the bound anti-IL4 antibodies to dissociate from the immobilized IL4 for 600 sec. Biosensors were regenerated and neutralized with 10 mM Glycine/HCl, pH 1.7 and D-PBS for 5 sec each, using three cycles before the first measurement and between all following measurements. Each assay was performed at 30° C. and 1000 rpm shaking with the sensor offset set to 3 mm and started after a delay of 600 sec to equilibrate the plate for 10 min (30° C. and shaking). All samples were measured in a double-referenced manner (as described in the Octet® $QK^e$ manual)—the two references being: (i) the supernatant of a mock transfection (1:10 in D-PBS) without bound ligand, and (ii) the supernatant of a mock transfection (1:10 in D-PBS) with bound IL4 ligand.

(b) Data Analysis of Antibody Binding Experiments

All sample data points were calculated using (i) the double references (see above) thereby correcting for non-specific binding and ligand dissociation, and (ii) interstep correction to avoid misalignment between two measurement steps (as described in the Octet® $QK^e$ manual). The resulting binding curves were fitted with a local full 1:1 model and the dissociation constant $k_{dis}$ calculated. Multiple data points from several transfections (each done in duplicate) were used to create mean values and standard deviations from three independent experiments.

Example 2: Results/Conclusions

The results of the luciferase experiments are shown in FIGS. 3 to 10, the results of the antibody experiments are shown in FIGS. 12 to 16.

Using both intracellularly expressed one-chain luciferase constructs and secreted two-chain antibody constructs it was shown that:

(a) Introducing various short and ultra-short introns into the coding sequence of various proteins led to functional proteins (cytosolic or secreted) when expressed in (eukaryotic) HEK293FS cells with similar expression levels as the control proteins without introns.
(b) Mutating the canonical splice sites led to a reduction of expression levels of the proteins of interest to the level of mock transfections as expected thus showing that a functional intron (and thus its removal from the pre-mRNA) is paramount to proper expression of a protein of interest.
(c) Introduction of two identical or non-identical introns led to expression levels comparable to those sequences containing only one intron.
(d) Insertions of "foreign" sequences into an intron led to good expression even if the expression levels of some of the proteins were slightly reduced when compared to control levels.
(e) Insertions of three to seven (identical or non-identical) introns showed no expression for some introns. All others showed reduced levels of expression.
(f) Introns may contain at least one internal in-frame stop codon to make sure that constructs that are not spliced do not give rise to an elongated protein that could still (but does not necessarily need to) possess the properties of the expected protein (after splicing)—e.g. in case the length of the intron is a multiple of three.
(g) Antibody constructs generated by modular, Golden Gate-based cloning which contained various combinations of introns were produced and secreted into the culture medium as expected albeit at varying expression levels depending on the intron combinations used in the constructs. Combinations of longer introns such as Intron 18 and 19 generally gave rise to higher expression levels than those containing an ultra-short intron. Functional tests of antibody constructs showed binding to their target in the expected range albeit in some but not all cases intron 13 or its modified form m13 displayed slightly reduced binding.

It was shown that introns can be used together with the Golden Gate cloning approach to create correctly folded proteins of interest by using the cellular splicing apparatus to produce functional mRNAs. The cloning method of the present invention is advantageous since it eliminates the necessity of DNA module-specific prefix and suffix sequences and thus allows the combination of otherwise incompatible DNA modules resulting in a fully generic and universal protein-engineering methodology. In contrast, in the cloning technologies described in the art, DNA modules of interest can only be linearly fused if they contain unique and compatible prefix-suffix pairs, and consequently, primary module sequences with incompatible prefix-suffix pairs must be modified by primary DNA sequence manipulation (e.g. by introducing compatible sequences) to allow for directional assembly. Compatible prefix and suffix sequences are made of complementary 4 base pair overhangs (prefix-suffix pairs) generated by type IIs restriction enzymes (e.g. BsaI). Consequently, protein modules can be joined by Golden Gate cloning at shared terminal 4 bp target sites (typically a common amino acid codon+1 additional nucleotide).

The method of the present invention, however, allows that DNA modules (e.g coding for protein domains) are assembled by cut and paste mechanisms using defined flanking prefix and suffix sequences coding for non-palindromic type IIs restriction sites. Here, prefix and suffix sequences for DNA module assembly are displaced from the terminal parts of the DNA modules and instead positioned at 3' or 5' termini of split intron sequences (e.g. functional introns that are divided into two, non-functional moieties) which are fused to the DNA modules of interest. Thus, prefix and suffix sequences are provided by the intron sequences. Generic assembly of DNA module without the prerequisite of compatible terminal prefix and suffix sequences being part of primary DNA sequence. No alterations of primary DNA sequence is required. Thus, a generic assembly of DNA modules without the prerequisite of compatible terminal prefix and suffix sequences being part of primary DNA sequence is possible. No alterations of primary DNA sequences are required. As prefix and suffix sequences are no longer part of primary DNA modules flexibility/variability for multi-domain assembly is achieved by i) shifting the position of the type IIs target site within the intron sequence or ii) by using alternative intron sequences or iii) a combination thereof.

The method of the present invention is advantageous because it allows the ligation of sequences (e.g. encoding protein domains) that share at least one identical stretch of three nucleotides at the overlap position, i.e. within the overhangs generated after cleavage. This allows for a flexible and coding sequence-independent ligation of DNA sequences. Accordingly, the present invention allows the ligation and thus the concatenation of coding sequences with flanking nucleic sequences sequences which are used/allow for ligation independent of the coding sequence.

The constructs assembled by the method can comprise artificial introns. It has been shown that the introns may be removed in an eukaryotic expression host by splicing to result in the intended polypeptide of interest although it became evident that the introns tested here cannot be combined arbitrarily. However, this was not unexpected. As it is known in the art, splicing is regulated by activating and inhibitory nucleotide sequences within both exons and introns (see e.g. Lee and Rio, Annu. Rev. Biochem. 2015. 84:291-323, or Yeo G W, Van Nostrand E L, Liang T Y (2007) Discovery and analysis of evolutionarily conserved intronic splicing regulatory elements. PLoS Genet 3(5): e85. doi:10.1371/journal.pgen.0030085). Although there is a large body of experimental data showing the influence of various short nucleotide sequences on splicing efficiency, not all regulatory sequences are known. Neither is their influence in a given sequence context always known. Furthermore, regulation of splicing may work differently for ultra-short introns than for longer introns. In the experiments described above it seemed as if splicing of ultra-short introns is more susceptible to potential regulatory elements than the longer introns used here.

Surprisingly, in many cases identical introns can be used at multiple positions within a construct without hampering the expression of the protein of interest.

The invention claimed is:

1. A method for producing a fusion polynucleotide encoding a polypeptide of interest, said method comprising the steps of:
- (a1) providing a first polynucleotide, said first polynucleotide comprising, in 5' to 3' direction,
  - (i) a nucleic acid sequence encoding a first portion of the polypeptide of interest,
  - (ii) a nucleic acid sequence encoding a 5' portion of a first intron,
  - (iii) a first cleavage sequence for a type IIs restriction endonuclease, and
  - (iv) a recognition sequence for the type IIs restriction endonuclease, wherein the first cleavage sequence in (iii) is operably linked to said recognition sequence,
- (a2) providing a second polynucleotide, said second polynucleotide comprising, in 5' to 3' direction,
  - (i) a recognition sequence for the type IIs restriction endonuclease,
  - (ii) a second cleavage sequence for the type IIs restriction endonuclease, wherein said second cleavage sequence is complementary to the first cleavage sequence, and wherein said second cleavage sequence is operably linked to the recognition sequence in (a2) (i),
(iii) a nucleic acid sequence encoding a 3' portion of the first intron,
(iv) a nucleic acid sequence encoding a second portion of the polypeptide of interest,
(v) a nucleic acid sequence encoding a 5' portion of a second intron,
(vi) a third cleavage sequence for the type IIs restriction endonuclease, which differs from the first cleavage sequence of the first polynucleotide, and
(vii) a recognition sequence for the type IIs restriction endonuclease, wherein said third cleavage sequence is operably linked to the recognition sequence in (a2)(vii), and
(a3) providing a third polynucleotide, said third polynucleotide comprising, in 5' to 3' direction,
(i) a recognition sequence for the type IIs restriction endonuclease,
(ii) to fourth cleavage sequence for the type IIs restriction endonuclease, wherein said fourth cleavage sequence is complementary to the third cleavage sequence, wherein the fourth cleavage sequence is operably linked to the recognition sequence in (a3) (i),
(iii) a nucleic acid sequence encoding a 3' portion of the second intron, and
(iv) a nucleic acid sequence encoding a third portion of the polypeptide of interest,
(b) contacting said first, second and third polynucleotides with the type IIs restriction endonuclease and a ligase under conditions that allow for cleavage of the first, second and third polynucleotide by said type IIs restriction endonuclease and ligation of the resulting cleavage products, thereby producing the fusion polynucleotide encoding the polypeptide of interest, and
wherein said fusion polynucleotide, when transcribed in a eukaryotic host cell, is transcribed into a mRNA transcript that is processed so that the type IIs restriction endonuclease cleavage and recognition sequences and the intron sequences are removed from the fusion polynucleotide by eukaryotic host cell splicing.

2. The method of claim 1, wherein said fusion polynucleotide comprises, in 5' to 3' direction:
(aa) the nucleic acid sequence encoding the first portion of the polypeptide of interest,
(bb) a nucleic acid sequence encoding the first intron, wherein said first intron is functional, and wherein said first intron comprises the nucleic acid sequence encoding the 5' portion of the first intron and the nucleic acid sequence encoding the 3' portion of the first intron,
(cc) the nucleic acid sequence encoding the second portion of the polypeptide of interest,
(dd) a nucleic acid sequence encoding the second intron, wherein said second intron is functional, and wherein said second intron comprises the nucleic acid sequence encoding the 5' portion of the second intron and the nucleic acid sequence encoding the 3' portion of the second intron, and
(ee) the nucleic acid sequence encoding the third portion of the polypeptide of interest.

3. The method of claim 1, wherein the first intron and/or the second intron is/are heterologous to the fusion polynucleotide.

4. The method of claim 1, wherein the polynucleotide encoding the first intron and/or the polynucleotide encoding the second intron has a length of 40 to 2000 bp.

5. The method of claim 1, wherein the polynucleotide encoding the first and/or second intron has a length of 50 to 200 bp.

6. The method of claim 1, wherein said first and/or second intron comprise(s) an internal stop codon in frame with the open reading frame of the fusion polynucleotide encoding the polypeptide of interest.

7. The method of claim 1, wherein said type IIs restriction endonuclease is selected from AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, and SfaNI.

8. A method for producing a fusion polynucleotide encoding a polypeptide of interest, comprising cleaving with a type IIs restriction endonuclease
(a1) the first polynucleotide as defined in claim 1,
(a2) the second polynucleotide as defined in claims 1, and
(a3) the third polynucleotide as defined in claim 1,
and
ligating the resulting cleavage products with a ligase,
wherein the type II restriction endonuclease and the ligase are provided in a composition.

9. The method of claim 5, wherein the polynucleotide encoding the first and/or second intron has a length of 50 to 150 bp.

10. The method of claim 1, wherein each of said introns has a length of 80 to 200 nucleotides.

11. The method according to claim 1, wherein all introns comprise an internal stop codon in frame with the open reading frame of the nucleic acid sequence encoding the polypeptide of interest.

12. The method according to claim 1, wherein the fusion polynucleotide comprises a 5' untranslated region (UTR) and/or a 3' UTR.

* * * * *

SEQUENCE LISTING

<160> NUMBER OF SEQ ID NOS: 47

<210> SEQ ID NO 1
<211> LENGTH: 56

```
<212> TYPE: DNA
<213> ORGANISM: Artificial Sequence
<220> FEATURE:
<223> OTHER INFORMATION: Intron I1

<400> SEQUENCE: 1
gtaaggtaag aattgaattt ctcagttgaa ggatgcttac actcttgtcc atctag          56

<210> SEQ ID NO 2
<211> LENGTH: 62
<212> TYPE: DNA
<213> ORGANISM: Artificial Sequence
<220> FEATURE:
<223> OTHER INFORMATION: Intron I2

<400> SEQUENCE: 2
gtgagtgggc caggggagag gtgccgtggg gctgggccga gctgaccctc atgtctccat      60
ag                                                                    62

<210> SEQ ID NO 3
<211> LENGTH: 65
<212> TYPE: DNA
<213> ORGANISM: Artificial Sequence
<220> FEATURE:
<223> OTHER INFORMATION: Intron I3

<400> SEQUENCE: 3
gtgagtgggc gccccggcgg ggtgggcagt gggcgggccc gagctgaccg caccccctccc    60 cacag                                                                 65

<210> SEQ ID NO 4
<211> LENGTH: 65
<212> TYPE: DNA
<213> ORGANISM: Artificial Sequence
<220> FEATURE:
<223> OTHER INFORMATION: Intron I4

<400> SEQUENCE: 4
gtaagggagg gaaggggggg tggggagggg ccggctgtgc cccccctcacc tgcccctccc    60 cacag                                                                 65

<210> SEQ ID NO 5
<211> LENGTH: 82
<212> TYPE: DNA
<213> ORGANISM: Artificial Sequence
<220> FEATURE:
<223> OTHER INFORMATION: Intron I5

<400> SEQUENCE: 5 gtaagggggtt aacagtagca ggcttgaggt ctggacatat atatgggtga caatgacatc    60
cactttgcct ttctctccac ag                                              82

<210> SEQ ID NO 6
<211> LENGTH: 375
<212> TYPE: DNA
<213> ORGANISM: Artificial Sequence
<220> FEATURE:
<223> OTHER INFORMATION: Intron I6

<400> SEQUENCE: 6
gtaagtcagg tgtcagccgc agatgcgttc aggtgagggc ggaggctagc ggggcgctgt     60
gcagcactga gctcgcggaa gaccaggacc aggagatcac cgagggcgac cgccaggccc    120
```

| | |
|---|---|
| cgggccctcc gctcccgagg ggcggcctct cagcaccagc ccgggggccg gcctgatcgc | 180 |
| cacgcaggca cctgccgccg ccaccgccac cgccatctca accgtacggg tgggagaggc | 240 |
| tgtgcgccgc tccaggggag atccggctcc catccggccc cacccgccct gccttgccct | 300 |
| gcccgcagct tctgggctgc caggctccat tctgaagctt ctactaactc tcgagtcttc | 360 |
| tttttttttt cacag | 375 |

```
<210> SEQ ID NO 7
<211> LENGTH: 72
<212> TYPE: RNA
<213> ORGANISM: Artificial Sequence
<220> FEATURE:
<223> OTHER INFORMATION: Intron I7

<400> SEQUENCE: 7
```

| | |
|---|---|
| gtaagtcaac gcaattaatc tatgaaatcc ctaatgccta cggcagccgc tggattgtta | 60 |
| cttcttcttc ag | 72 |

```
<210> SEQ ID NO 8
<211> LENGTH: 110
<212> TYPE: DNA
<213> ORGANISM: Artificial Sequence
<220> FEATURE:
<223> OTHER INFORMATION: Intron I8

<400> SEQUENCE: 8
```

| | |
|---|---|
| gtaagaacca aaccctccca gcagggggtgc ccaggcccag gcatggccca gagggagcag | 60 |
| cgggtggggc ttaggccaag ctgagctcac accttgacct ttcattccag | 110 |

```
<210> SEQ ID NO 9
<211> LENGTH: 82
<212> TYPE: DNA
<213> ORGANISM: Artificial Sequence
<220> FEATURE:
<223> OTHER INFORMATION: Intron I9

<400> SEQUENCE: 9
```

| | |
|---|---|
| gtgagtacag gaggtggaga gtggccagcc cttctcatgt tcagagaaca tggttaactg | 60 |
| gttaagtcat gtcgtcccac ag | 82 |

```
<210> SEQ ID NO 10
<211> LENGTH: 62
<212> TYPE: DNA
<213> ORGANISM: Artificial Sequence
<220> FEATURE:
<223> OTHER INFORMATION: Intron I2(del5ss)

<400> SEQUENCE: 10
```

| | |
|---|---|
| tggagtgggc caggggagag gtgccgtggg gctgggccga gctgaccctc atgtctccat | 60 |
| ag | 62 |

```
<210> SEQ ID NO 11
<211> LENGTH: 62
<212> TYPE: DNA
<213> ORGANISM: Artificial Sequence
<220> FEATURE:
<223> OTHER INFORMATION: Intron I2(del3ss)

<400> SEQUENCE: 11
```

| | |
|---|---|
| gtgagtgggc caggggagag gtgccgtggg gctgggccga gctgaccctc atgtctccat | 60 |
| ga | 62 |

<210> SEQ ID NO 12
<211> LENGTH: 65
<212> TYPE: DNA
<213> ORGANISM: Artificial Sequence
<220> FEATURE:
<223> OTHER INFORMATION: Intron I3(del5ss)

<400> SEQUENCE: 12
tggagtgggc gccccggcgg ggtgggcagt gggcgggccc gagctgaccg caccccctccc    60 cacag                                                                 65

<210> SEQ ID NO 13
<211> LENGTH: 65
<212> TYPE: DNA
<213> ORGANISM: Artificial Sequence
<220> FEATURE:
<223> OTHER INFORMATION: Intron I3(del3ss)

<400> SEQUENCE: 13
gtgagtgggc gccccggcgg ggtgggcagt gggcgggccc gagctgaccg caccccctccc    60 cacga                                                                 65

<210> SEQ ID NO 14
<211> LENGTH: 69
<212> TYPE: DNA
<213> ORGANISM: Artificial Sequence
<220> FEATURE:
<223> OTHER INFORMATION: Intron I3(ins38)-1

<400> SEQUENCE: 14
gtgagtgggc gccccggcgg ggtgggcagt gggcgggcaa gcccgagctg accgcacccc    60
tccccacag                                                             69

<210> SEQ ID NO 15
<211> LENGTH: 69
<212> TYPE: DNA
<213> ORGANISM: Artificial Sequence
<220> FEATURE:
<223> OTHER INFORMATION: Intron I3(ins38)-2

<400> SEQUENCE: 15
gtgagtgggc gccccggcgg ggtgggcagt gggcgggcag ccccgagctg accgcacccc    60
tccccacag                                                             69

<210> SEQ ID NO 16
<211> LENGTH: 69
<212> TYPE: DNA
<213> ORGANISM: Artificial Sequence
<220> FEATURE:
<223> OTHER INFORMATION: Intron I3(ins38)-3

<400> SEQUENCE: 16
gtgagtgggc gccccggcgg ggtgggcagt gggcgggttc ccccgagctg accgcacccc    60
tccccacag                                                             69

<210> SEQ ID NO 17
<211> LENGTH: 79
<212> TYPE: DNA
<213> ORGANISM: Artificial Sequence
<220> FEATURE:
<223> OTHER INFORMATION: Intron I3(ins38)-4

<400> SEQUENCE: 17
gtgagtgggc gccccggcgg ggtgggcagt gggcgggcaa gtgggctgag gcccgagctg    60
accgcacccc tccccacag                                                 79

<210> SEQ ID NO 18
<211> LENGTH: 79
<212> TYPE: DNA
<213> ORGANISM: Artificial Sequence
<220> FEATURE:
<223> OTHER INFORMATION: Intron I3(ins38)-5

<400> SEQUENCE: 18
gtgagtgggc gccccggcgg ggtgggcagt gggcgggcag ctgggctgct tcccgagctg    60
accgcacccc tccccacag                                                 79

<210> SEQ ID NO 19
<211> LENGTH: 69
<212> TYPE: DNA
<213> ORGANISM: Artificial Sequence
<220> FEATURE:
<223> OTHER INFORMATION: Intron I3(ins37)-1

<400> SEQUENCE: 19
gtgagtgggc gccccggcgg ggtgggcagt gggcggcaag gcccgagctg accgcacccc    60
tccccacag                                                            69

<210> SEQ ID NO 20
<211> LENGTH: 69
<212> TYPE: DNA
<213> ORGANISM: Artificial Sequence
<220> FEATURE:
<223> OTHER INFORMATION: Intron I3(ins37)-2

<400> SEQUENCE: 20
gtgagtgggc gccccggcgg ggtgggcagt gggcggcagc gcccgagctg accgcacccc    60
tccccacag                                                            69

<210> SEQ ID NO 21
<211> LENGTH: 115
<212> TYPE: DNA
<213> ORGANISM: Artificial Sequence
<220> FEATURE:
<223> OTHER INFORMATION: Intron I3(1-29)_I8(25-110)

<400> SEQUENCE: 21
gtgagtgggc gccccggcgg ggtgggcagg ggtgcccagg cccaggcatg gcccagaggg    60
agcagcgggt ggggcttagg ccaagctgag ctcacacctt gacctttcat tccag         115

<210> SEQ ID NO 22
<211> LENGTH: 60
<212> TYPE: DNA
<213> ORGANISM: Artificial Sequence
<220> FEATURE:
<223> OTHER INFORMATION: Intron I3(1-48)_I8(99-110)

<400> SEQUENCE: 22
gtgagtgggc gccccggcgg ggtgggcagt gggcgggccc gagctgacct ttcattccag    60

<210> SEQ ID NO 23
<211> LENGTH: 60
<212> TYPE: DNA
<213> ORGANISM: Artificial Sequence

```
<220> FEATURE:
<223> OTHER INFORMATION: Intron I8(1-24)_I3(30-65)

<400> SEQUENCE: 23
gtaagaacca aaccctccca gcagtgggcg ggcccgagct gaccgcaccc ctccccacag      60

<210> SEQ ID NO 24
<211> LENGTH: 115
<212> TYPE: DNA
<213> ORGANISM: Artificial Sequence
<220> FEATURE:
<223> OTHER INFORMATION: Intron I8(1-98)_I3(49-65)

<400> SEQUENCE: 24
gtaagaacca aaccctccca gcagggtgc ccaggcccag gcatggccca gagggagcag       60
cgggtggggc ttaggccaag ctgagctcac accttgaccg caccctccc cacag           115

<210> SEQ ID NO 25
<211> LENGTH: 29
<212> TYPE: DNA
<213> ORGANISM: Artificial Sequence
<220> FEATURE:
<223> OTHER INFORMATION: I3N1(1-29)

<400> SEQUENCE: 25
gtgagtgggc gccccggcgg ggtgggcag                                        29

<210> SEQ ID NO 26
<211> LENGTH: 36
<212> TYPE: DNA
<213> ORGANISM: Artificial Sequence
<220> FEATURE:
<223> OTHER INFORMATION: I3C1(30-65)

<400> SEQUENCE: 26
tgggcgggcc cgagctgacc gcaccctcc ccacag                                 36

<210> SEQ ID NO 27
<211> LENGTH: 48
<212> TYPE: DNA
<213> ORGANISM: Artificial Sequence
<220> FEATURE:
<223> OTHER INFORMATION: I3N2(1-48)

<400> SEQUENCE: 27
gtgagtgggc gccccggcgg ggtgggcagt gggcgggccc gagctgac                   48

<210> SEQ ID NO 28
<211> LENGTH: 17
<212> TYPE: DNA
<213> ORGANISM: Artificial Sequence
<220> FEATURE:
<223> OTHER INFORMATION: I3C2(49-65)

<400> SEQUENCE: 28 cgcaccctc cccacag                                                      17

<210> SEQ ID NO 29
<211> LENGTH: 40
<212> TYPE: DNA
<213> ORGANISM: Artificial Sequence
<220> FEATURE:
<223> OTHER INFORMATION: mI3N1(1-36_insCAAG)

<400> SEQUENCE: 29
```
gtgagtgggc gccccggcgg ggtgggcagt gggcggcaag                              40

<210> SEQ ID NO 30
<211> LENGTH: 29
<212> TYPE: DNA
<213> ORGANISM: Artificial Sequence
<220> FEATURE:
<223> OTHER INFORMATION: mI3C1(insCAAG_37-65)

<400> SEQUENCE: 30
gcccgagctg accgcacccc tccccacag                                         29

<210> SEQ ID NO 31
<211> LENGTH: 40
<212> TYPE: DNA
<213> ORGANISM: Artificial Sequence
<220> FEATURE:
<223> OTHER INFORMATION: mI3N2(1-36_insCAGC)

<400> SEQUENCE: 31
gtgagtgggc gccccggcgg ggtgggcagt gggcggcagc                              40

<210> SEQ ID NO 32
<211> LENGTH: 29
<212> TYPE: DNA
<213> ORGANISM: Artificial Sequence
<220> FEATURE:
<223> OTHER INFORMATION: mI3C2(insCAGC_37-65)

<400> SEQUENCE: 32
gcccgagctg accgcacccc tccccacag                                         29

<210> SEQ ID NO 33
<211> LENGTH: 24
<212> TYPE: DNA
<213> ORGANISM: Artificial Sequence
<220> FEATURE:
<223> OTHER INFORMATION: I8N1(1-24)

<400> SEQUENCE: 33
gtaagaacca aaccctccca gcag                                              24

<210> SEQ ID NO 34
<211> LENGTH: 86
<212> TYPE: DNA
<213> ORGANISM: Artificial Sequence
<220> FEATURE:
<223> OTHER INFORMATION: I8C1(25-110)

<400> SEQUENCE: 34
gggtgcccag gcccaggcat ggcccagagg gagcagcggg tggggcttag gccaagctga       60
gctcacacct tgacctttca ttccag                                            86

<210> SEQ ID NO 35
<211> LENGTH: 98
<212> TYPE: DNA
<213> ORGANISM: Artificial Sequence
<220> FEATURE:
<223> OTHER INFORMATION: I8N2(1-98)

<400> SEQUENCE: 35
gtaagaacca aaccctccca gcaggggtgc ccaggcccag gcatggccca gagggagcag       60
cgggtggggc ttaggccaag ctgagctcac accttgac                               98

```
<210> SEQ ID NO 36
<211> LENGTH: 12
<212> TYPE: DNA
<213> ORGANISM: Artificial Sequence
<220> FEATURE:
<223> OTHER INFORMATION: I8C2(99-110)

<400> SEQUENCE: 36
ctttcattcc ag                                                          12

<210> SEQ ID NO 37
<211> LENGTH: 22
<212> TYPE: DNA
<213> ORGANISM: Artificial Sequence
<220> FEATURE:
<223> OTHER INFORMATION: I9N1(1-22)

<400> SEQUENCE: 37
gtgagtacag gaggtggaga gt                                               22

<210> SEQ ID NO 38
<211> LENGTH: 59
<212> TYPE: DNA
<213> ORGANISM: Artificial Sequence
<220> FEATURE:
<223> OTHER INFORMATION: I9C1(23-82)

<400> SEQUENCE: 38
ggccagccct tctcatgttc agagaacatg gttaactggt taagtcatgt cgtcccaca       59

<210> SEQ ID NO 39
<211> LENGTH: 60
<212> TYPE: DNA
<213> ORGANISM: Artificial Sequence
<220> FEATURE:
<223> OTHER INFORMATION: I9N2(1-60)

<400> SEQUENCE: 39
gtgagtacag gaggtggaga gtggccagcc cttctcatgt tcagagaaca tggttaactg       60

<210> SEQ ID NO 40
<211> LENGTH: 22
<212> TYPE: DNA
<213> ORGANISM: Artificial Sequence
<220> FEATURE:
<223> OTHER INFORMATION: I9C2(61-82)

<400> SEQUENCE: 40
gttaagtcat gtcgtcccac ag                                               22

<210> SEQ ID NO 41
<211> LENGTH: 14
<212> TYPE: DNA
<213> ORGANISM: Artificial Sequence
<220> FEATURE:
<223> OTHER INFORMATION: hRluc - I3 modified 1

<400> SEQUENCE: 41
caagtgggct gagg                                                        14

<210> SEQ ID NO 42
<211> LENGTH: 14
<212> TYPE: DNA
<213> ORGANISM: Artificial Sequence
<220> FEATURE:
<223> OTHER INFORMATION: hRluc - I3 modified 2
```

```
<400> SEQUENCE: 42
cagctgggct gctt                                                          14

<210> SEQ ID NO 43
<211> LENGTH: 15
<212> TYPE: DNA
<213> ORGANISM: Artificial Sequence
<220> FEATURE:
<223> OTHER INFORMATION: consensus Kozak sequence, vector

<400> SEQUENCE: 43
cacgtgagcg ccacc                                                         15

<210> SEQ ID NO 44
<211> LENGTH: 31
<212> TYPE: DNA
<213> ORGANISM: Artificial Sequence
<220> FEATURE:
<223> OTHER INFORMATION: DNA sequence, vector

<400> SEQUENCE: 44
actttgtaca aaaaagcagg ctagcgccac c                                       31

<210> SEQ ID NO 45
<211> LENGTH: 31
<212> TYPE: DNA
<213> ORGANISM: Artificial Sequence
<220> FEATURE:
<223> OTHER INFORMATION: DNA sequence, vector

<400> SEQUENCE: 45
tgataagctt acccagcttt cttgtacaaa g                                       31

<210> SEQ ID NO 46
<211> LENGTH: 12
<212> TYPE: DNA
<213> ORGANISM: Artificial Sequence
<220> FEATURE:
<223> OTHER INFORMATION: sequence flanked by BsaI sites, vector

<400> SEQUENCE: 46
cgccaggaga cc                                                            12

<210> SEQ ID NO 47
<211> LENGTH: 12
<212> TYPE: DNA
<213> ORGANISM: Artificial Sequence
<220> FEATURE:
<223> OTHER INFORMATION: sequence flanked by BsaI sites, vector

<400> SEQUENCE: 47
ggtctctata at                                                            12
```